US012758239B2

(12) United States Patent
Su et al.

(10) Patent No.: US 12,758,239 B2
(45) Date of Patent: Oct. 13, 2026

(54) CATHETER TIP FOR ASPIRATION SYSTEM

(71) Applicant: Walk Vascular, LLC, Irvine, CA (US)

(72) Inventors: Ted Su, Sunnyvale, CA (US); Jared Ryan G. Lumauig, San Jose, CA (US); Connie Vien Cheng, San Jose, CA (US); Seung Hae Clare Chung, Los Altos, CA (US); Grant A. Adams, New Brighton, MN (US); Rafael A. Castellanos Alvarez, San Jose, CA (US); Randolf von Oepen, Aptos, CA (US)

(73) Assignee: Walk Vascular, LLC, Irvine, CA (US)

(*) Notice: Subject to any disclaimer, the term of this patent is extended or adjusted under 35 U.S.C. 154(b) by 28 days.

(21) Appl. No.: 18/976,691

(22) Filed: Dec. 11, 2024

(65) Prior Publication Data

US 2025/0195091 A1 Jun. 19, 2025

Related U.S. Application Data

(60) Provisional application No. 63/611,500, filed on Dec. 18, 2023.

(51) Int. Cl.

*A61B 17/22* (2006.01)
*A61B 17/00* (2006.01)

(52) U.S. Cl.

CPC ........ *A61B 17/22* (2013.01); *A61B 17/00234* (2013.01); *A61B 2017/00238* (2013.01); *A61B 2017/00305* (2013.01); *A61B 2017/00557* (2013.01); *A61B 2017/00862* (2013.01); *A61B 2017/00867* (2013.01); *A61B 2017/00946* (2013.01); *A61B 2017/22079* (2013.01); *A61B 2217/005* (2013.01); *A61B 2217/007* (2013.01)

(58) Field of Classification Search

CPC .............. A61B 17/22; A61B 17/22012; A61B 17/32037; A61B 2017/22079; A61B 2017/22084; A61M 25/0067; A61M 25/0074

See application file for complete search history.

(56) References Cited

U.S. PATENT DOCUMENTS

| | | | | |
|---|---|---|---|---|
| 4,140,119 | A * | 2/1979 | Pollack | A61M 25/0068 604/27 |
| 11,376,028 | B1 * | 7/2022 | Saadat | A61B 17/320758 |
| 2009/0270800 | A1 * | 10/2009 | Spurchise | A61M 25/0074 604/95.04 |
| 2014/0074144 | A1 * | 3/2014 | Shrivastava | A61B 17/221 606/200 |
| 2019/0209745 | A1 | 7/2019 | Hanson et al. | |
| 2020/0246014 | A1 | 8/2020 | Walzman | |
| 2022/0175404 | A1 | 6/2022 | Mintz et al. | |
| 2023/0240694 | A1 | 8/2023 | Panian | |
| 2025/0057548 | A1 * | 2/2025 | Hanson | A61M 25/0074 |

FOREIGN PATENT DOCUMENTS

| | | | |
|---|---|---|---|
| WO | 2025/038591 | A1 | 2/2025 |

* cited by examiner

*Primary Examiner* — Diane D Yabut
(74) *Attorney, Agent, or Firm* — Workman Nydegger

(57) ABSTRACT

Disclosed are embodiments of an aspiration catheter comprising a tissue encroachment prevent assembly for preventing vessel tissue from being drawn into the aspiration lumen and/or into close proximity to an injection of pressurized fluid from a supply lumen during aspiration of a thrombus.

20 Claims, 17 Drawing Sheets

CATHETER TIP FOR ASPIRATION SYSTEM

CROSS-REFERENCE TO RELATED APPLICATIONS

This application claims priority to and the benefit of U.S. Provisional Patent Application Ser. No. 63/611,500, filed Dec. 18, 2023, and entitled "CATHETER TIP FOR ASPIRATION SYSTEM," the disclosure of which is incorporated herein by this reference.

BACKGROUND OF THE INVENTION

Technical Field

The present disclosure pertains generally to medical devices and methods of their use. More particularly, the present invention pertains to aspiration and thrombectomy devices and methods of use thereof.

Description of the Related Art

Several devices and systems already exist to aid in the removal of thrombotic material. These include simple aspiration tube type devices using vacuum syringes to extract thrombus into the syringe, simple flush-and-aspirate devices, more complex devices with rotating components that pull in, macerate and transport thrombotic material away from the distal tip using a mechanical auger, and systems that use very high pressure to macerate the thrombus and create a venturi effect to flush the macerated material away.

All of the devices described above have limitations as a result of individual design characteristics. For example, simple aspiration catheters offer ease of use and rapid deployment but may become blocked or otherwise inoperable when faced with older, more organized thrombotic material. Such devices must be removed and cleared outside the body and then re-inserted into the vasculature, which lengthens the time needed for the procedure and increases the opportunity to kink the catheter shaft. Such kinks may reduce performance by decreasing the cross-sectional area of the catheter or may render the device inoperable.

Mechanical rotary devices use an auger to grab and carry the thrombus away from the target area. Some create transport force via vacuum bottles while others create differential pressure at the distal tip of the device with the auger acting as a low-pressure pump. These devices typically work slowly and offer the physician no feedback as to when the device should be advanced further into the lesion.

Flushing type devices include manual flush type devices in which the physician manipulates a hand-driven pump to provide flowing saline at the tip of the device to break up and aspirate the thrombus material, which may introduce performance variations based on the ability of the physician to consistently pump the device over the duration of the procedure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods, and devices for aspirating thrombus or material within a patient's body.

Implementations of the present invention solve one or more problems in the art with systems, methods, and devices for aspirating thrombus or material within a patient's body. For instance, the present invention relates to aspiration catheters that prevent vessel tissue from being drawn into an aspiration lumen of the aspiration catheter and coming into close proximity to an orifice for jetted fluid from a supply lumen during aspiration. A system for aspirating thrombus, comprising an aspiration catheter including an elongate shaft configured for placement within a blood vessel of a subject, a supply lumen, an aspiration lumen each extending along the shaft, and an opening (or "orifice") at or near the distal end of the supply lumen, the opening configured to allow the injection of pressurized fluid into the aspiration lumen at or near the distal end of the aspiration lumen when the pressurized fluid is caused or allowed to flow through the supply lumen; a tubing set comprising a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source; a pressurization element configured to couple to the tubing set and further configured to pressurize fluid from the first fluid source or allow pressurized fluid from the first fluid source to be transferred to the supply lumen, such that the pressurized fluid is capable of flowing through the supply lumen from the proximal end of the supply lumen to the distal end of the supply lumen; and wherein the vacuum source comprises a vacuum canister having two or more ports, including a first port configured to couple to a proximal end of the first conduit of the tubing set, and wherein the vacuum canister is configured to separate thrombus from aspirant delivered via the first conduit of the tubing set.

In another configuration, the aspiration catheter may also include a tip configured to prevent the distal end opening of the catheter—and, more specifically, the distal opening of the aspiration lumen—from coming into contact with the vessel wall during aspiration. Such tip may comprise a wide mouth tip which prevents an orifice in the supply lumen which is configured for injection of pressurized fluid from coming into contact with the vessel wall if the vessel wall is drawn into the aspiration lumen during aspiration.

In another configuration, the aspiration catheter comprises an elongate shaft configured for placement within a blood vessel, a supply lumen and an aspiration lumen each extending along the shaft, the supply lumen having a proximal end and a distal end, and the aspiration lumen having a proximal end and a distal opening, an orifice at or near the distal end of the supply lumen, the orifice being configured to allow injection of pressurized fluid into the aspiration lumen at or near the distal end of the aspiration lumen when the pressurized fluid is delivered through the supply lumen, and a tissue encroachment prevention assembly for preventing the blood vessel from being drawn into said aspiration lumen and coming into close proximity to the orifice of the supply lumen during aspiration.

In another configuration, the aspiration catheter comprises an elongate shaft configured for placement within a blood vessel, the elongate shaft having a distal end with an opening at the distal end, a supply lumen and an aspiration lumen each extending along the shaft, the supply lumen having a proximal end and a distal end, and the aspiration lumen having a proximal end and a distal opening, an orifice near the distal end of the supply lumen, the orifice being configured to allow injection of pressurized fluid into the aspiration lumen at or near the distal end of the aspiration lumen when the pressurized fluid is delivered through the supply lumen, and a means for preventing the blood vessel from being drawn into the aspiration lumen and into close proximity to the orifice of the supply lumen during aspiration.

In still another configuration, the aspiration catheter comprises an elongate shaft configured for placement within a blood vessel, the elongate shaft having a distal end with an opening at the distal end, a supply lumen and an aspiration lumen each extending along an interior of the shaft, coextensive with the shaft, the supply lumen having a proximal end and a distal end, and the aspiration lumen having a proximal end and a distal opening, an orifice near the distal end of the supply lumen, the orifice being configured to allow injection of pressurized fluid into the aspiration lumen at or near the distal end of the aspiration lumen when the pressurized fluid is pumped through the supply lumen; and a tissue encroachment prevention assembly for preventing the blood vessel from being drawn into the aspiration lumen and into close proximity to the orifice of the supply lumen during aspiration, the tissue encroachment prevention assembly comprising at least one of a wide-mouth tip and an expandable member located at or near the distal end of the aspiration catheter.

In another configuration, a system for aspirating thrombus comprises an aspiration catheter comprising an elongate shaft configured for placement within a blood vessel of a subject, a supply lumen and an aspiration lumen each extending along an interior of the elongate shaft, and an orifice at or near a distal end of the supply lumen, the orifice being configured to allow the injection of pressurized fluid into the aspiration lumen at or near the distal end of the aspiration lumen when the pressurized fluid is caused or allowed to flow through the supply lumen. The system also includes a tubing set comprising a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source. A pressurization element of the system is configured to couple to the tubing set and further configured to pressurize fluid from the first fluid source or allow pressurized fluid from the first fluid source to be transferred to the supply lumen, such that the pressurized fluid is capable of flowing through the supply lumen from the proximal end of the supply lumen to the orifice at or near the distal end of the supply lumen. A means for preventing the blood vessel from being drawn into the aspiration lumen and into close proximity to the orifice of the supply lumen during aspiration is also included.

In another configuration, a system for aspirating thrombus comprise an aspiration catheter comprising an elongate shaft configured for placement within a blood vessel of a subject, a supply lumen and an aspiration lumen each extending along an interior of the elongate shaft, and an orifice at or near a distal end of the supply lumen, the orifice being configured to allow the injection of pressurized fluid into the aspiration lumen at or near the distal end of the aspiration lumen when the pressurized fluid is caused or allowed to flow through the supply lumen. The system also includes a tubing set comprising a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source. A pressurization element and a tissue encroachment prevention assembly are also included in the system. The pressurization element is configured to couple to the tubing set and further configured to pressurize fluid from the first fluid source or allow pressurized fluid from the first fluid source to be transferred to the supply lumen, such that the pressurized fluid is capable of flowing through the supply lumen from the proximal end of the supply lumen to the orifice at or near the distal end of the supply lumen. The tissue encroachment prevention assembly is configured to prevent the blood vessel from being drawn into the aspiration lumen and into close proximity to the orifice of the supply lumen during aspiration.

In another configuration, an aspiration catheter comprises an elongate shaft configured for placement within a blood vessel, a supply lumen and an aspiration lumen each extending along an interior of the shaft, coextensive with the shaft, the supply lumen having a proximal end and a distal end, and the aspiration lumen having a proximal end and a distal opening, an orifice at or near the distal end of the supply lumen, the orifice configured to allow injection of pressurized fluid into the aspiration lumen at or near the distal end of the aspiration lumen when the pressurized fluid is pumped through the supply lumen, and a means for preventing the blood vessel from being drawn into said aspiration lumen and coming into close proximity to the orifice of the supply lumen during aspiration, said means comprising a wide mouth tip located at or near the distal end of the aspiration catheter, the tip having a proximal end attached to the aspiration catheter and a distal opening, wherein the distal opening of the wide mouth tip has an inner diameter that is larger than the inner diameter of the aspiration lumen.

In another configuration, an aspiration catheter comprises an elongate shaft configured for placement within a blood vessel, a supply lumen and an aspiration lumen each extending along an interior of the shaft, coextensive with the shaft, the supply lumen having a proximal end and a distal end, and the aspiration lumen having a proximal end and a distal opening, an orifice at or near the distal end of the supply lumen, the orifice configured to allow injection of pressurized fluid into the aspiration lumen at or near the distal end of the aspiration lumen when the pressurized fluid is pumped through the supply lumen, and a means for preventing the blood vessel from being drawn into said aspiration lumen and coming into close proximity to the orifice of the supply lumen during aspiration. The means comprising an expandable member located at or near the distal end of the aspiration catheter, the expandable member having a proximal end attached to the aspiration catheter and a distal opening. Wherein the distal opening of the expandable member has an inner diameter that is larger than the inner diameter of the aspiration lumen when the expandable member is in an inflated state.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Figure 1:
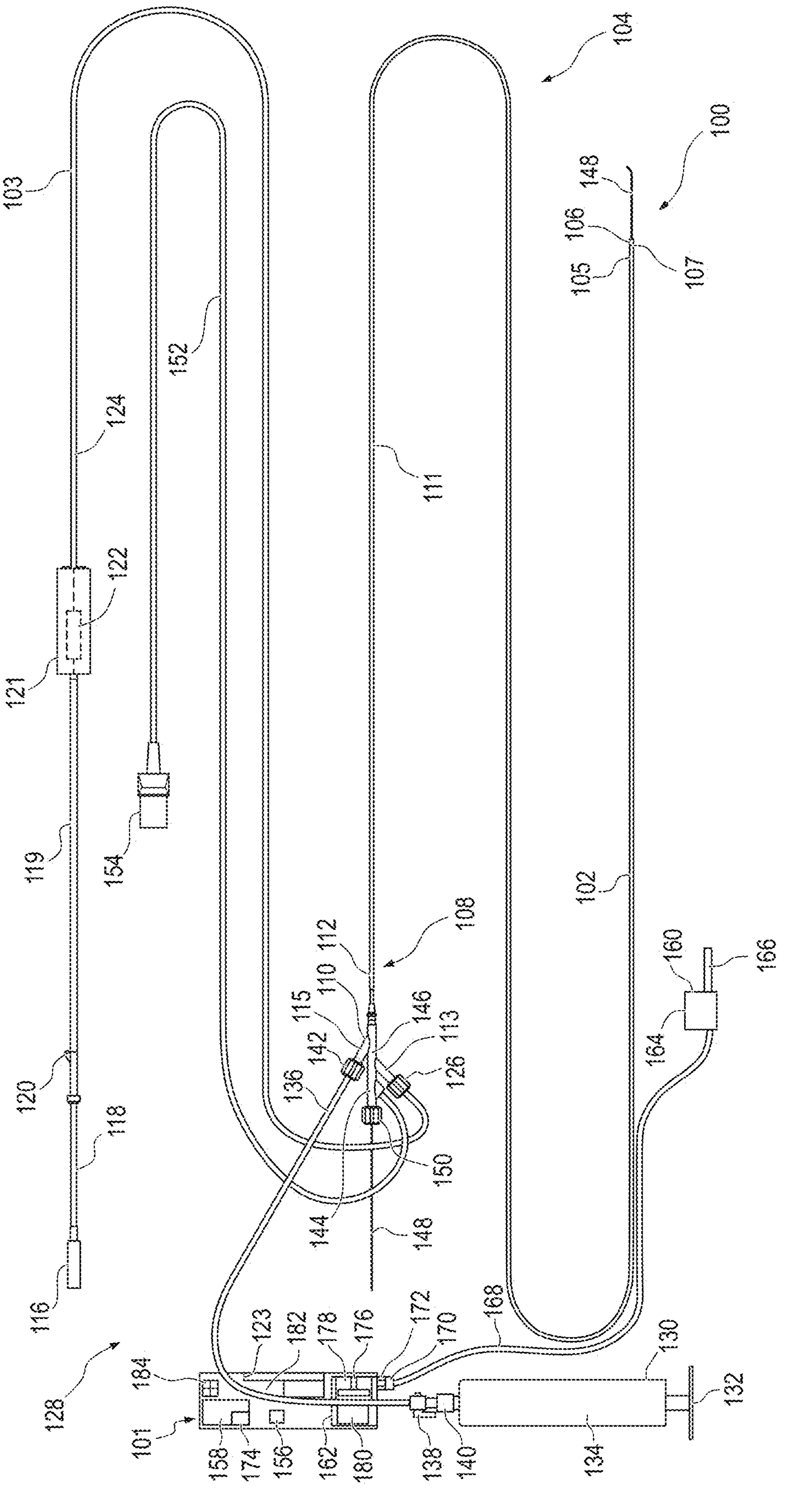
FIG. 1 is a plan view of exemplary disposable components of a system for aspirating thrombus according to an implementation of the present disclosure.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to preventing tissue, such as tissue of a lumen receiving an aspiration catheter, from being drawn into an aspiration lumen of the aspiration catheter and coming into close proximity to an orifice for jetted fluid from a supply lumen during aspiration. By preventing the tissue from being brought towards the fluid jetted or ejected from the orifice through the tissue encroachment prevention assembly—i.e., a means for preventing the blood vessel from being drawn into the aspiration lumen—tissue damage is prevented during aspiration of thrombus. Thus, the aspiration process is safer for a patient.

While the present disclosure will describe a particular implementation of preventing tissue from being drawn into an aspiration lumen of the aspiration catheter and coming into close proximity to an orifice for jetted fluid from a supply lumen during aspiration, it should be understood that the devices, systems, and method described herein may be applicable to other uses. Additionally, elements described in relation to any embodiment depicted and/or described herein may be combinable with elements described in relation to any other embodiment depicted and/or described herein.

A system 100 for aspirating thrombus is illustrated in FIGS. 1-5. The system 100 for aspirating thrombus includes a pump 101, an aspiration catheter 102, and a tubing set 103. The aspiration catheter 102 and the tubing set 103 represent disposable components 104, and the pump 101, and the pump's associated pump base, is a reusable component. It is not necessary to sterilize the pump 101 as it may be kept in a non-sterile field or area during use. The aspiration catheter 102 and the tubing set 103 may each be supplied sterile, after sterilization by ethylene oxide gas, electron beam, gamma, or other sterilization methods. The aspiration catheter 102 may be packaged and supplied separately from the tubing set 103, or the aspiration catheter 102 and the tubing set 103 may be packaged together and supplied together. Alternatively, the aspiration catheter 102 and tubing set 103 may be packaged separately, but supplied together (i.e., bundled).

The aspiration catheter 102 has a distal end 105 and includes an over-the-wire guidewire lumen/aspiration lumen 106 extending between an open distal end 107, and a proximal end 108 comprising a y-connector 110. The catheter shaft 111 of the aspiration catheter 102 is connected to the y-connector 110 via a protective strain relief 112. In other embodiments, the catheter shaft 111 may be attached to the y-connector 110 with a luer fitting. The y-connector 110 includes a first female luer 113 which communicates with a catheter supply lumen 114 (FIG. 2), and a second female luer 115 which communicates with the guidewire lumen/aspiration lumen 106. While reference is made to the y-connector 110 communicating with the supply lumen 114 (FIG. 2), it will be understood that one or more supply lumens 114 can be included and the y-connector 110, or other connectors, can communicate with the one or more supply lumens 114.

A spike 116 for coupling to a fluid source 224 (e.g., saline bag, saline bottle) allows fluid to enter through an extension tubing 118 and flow into a supply tube 119. An optional injection port 120 allows injection of materials or removal of air. A cassette 121 having a moveable piston 122 is used in conjunction with a mechanical actuator 123 of the pump 101. Fluid is pumped into an injection tube 124 from action of the cassette 121 as applied by the actuator 123 of the pump 101. A male luer 126, hydraulically communicating with the catheter supply lumen 114, via the injection tube 124, is configured to attach to the female luer 113 of the y-connector 110.

Accessories 128 are illustrated that are intended for applying a vacuum source, such as a syringe 130 having a plunger 132 and a barrel 134, to the aspiration lumen 106 of the aspiration catheter 102. The syringe 130 is attached to a vacuum line 136 via the luer 140 of the syringe 130. A stopcock 138 may be used on the luer 140 to maintain the vacuum, or alternatively, the plunger 132 may be a locking variety of plunger that is configured to be locked in the retracted (vacuum) position. A male luer 142 at the end of the vacuum line 136 may be detachably secured to the female luer 115 of the y-connector 110 of the aspiration catheter 102. As shown in more detail in FIG. 3, a pressure sensor or transducer 144 is secured inside an internal cavity 146 of the y-connector 110 proximal to the female luer 113 and the female luer 115. A valve 150, for example a Touhy-Borst, at the proximal end of the y-connector 110 allows hemostasis of the guidewire lumen/aspiration lumen 106 around a guidewire 148. In other embodiments, the valve 150 may comprise a longitudinally spring-loaded seal. The guidewire 148 may be inserted entirely through the guidewire lumen/aspiration lumen 106. Signals output from the pressure sensor 144 are carried through a cable 152 to a connector 154. The connector 154 is plugged into a socket 156 of the pump 101. Pressure related signals may be processed by a circuit board 158 of the pump 101. The pressure sensor or transducer 144 may be powered from the pump 101, via the cable 152. The accessories 128 may also be supplied sterile to the user.

A foot pedal 160 is configured to operate a pinch valve 162 for occluding or opening the vacuum line 136. The foot pedal 160 comprises a base 164 and a pedal 166 and is configured to be placed in a non-sterile area, such as on the floor, under the procedure table/bed. The user steps on the pedal 166 causing a signal to be sent along a cable 168 which is connected via a plug 170 to an input jack 172 in the pump 101. The vacuum line 136 extends through a portion of the pump 101. The circuit board 158 of the pump may include a controller 174 configured to receive one or more signals indicating on or off from the foot pedal 160. The controller 174 of the circuit board 158 may be configured to cause an actuator 176 carried by the pump 101 to move longitudinally to compress and occlude the vacuum line 136 between an actuator head 178 attached to the actuator 176 and an anvil 180, also carried by the pump 101. By stepping on the pedal 166, the user is able to thus occlude the vacuum line 136, stopping the application of a negative pressure. In some embodiments, as the pedal 166 of the foot pedal 160 is depressed, the controller may be configured to open the pinch valve 162.

The pressure sensor or transducer 144 thus senses a negative pressure and sends a signal, causing the controller to start the motor 182 of the pump 101. As the effect via the electronics is substantially immediate, the motor 182 starts pumping almost immediately after the pedal 166 is depressed. As the pedal 166 of the foot pedal 160 is released, the controller 174 then causes the pinch valve 162 to close. The pressure sensor or transducer 144 thus senses that no negative pressure is present and the controller 174 causes the motor 182 of the pump 101 to shut off. Again, the effect via the electronics is substantially immediate, and thus the motor 182 stops pumping almost immediately after the pedal 166 is released. During sterile procedures, the main interventionalist is usually "scrubbed" such that the hands only touch items in the sterile field. However, the feet/shoes/shoe covers are not in the sterile field. Thus again, a single user may operate a switch (via the pedal 166) while also manipulating the aspiration catheter 102 and guidewire 148. However, this time, it is the sterile field hands and non-sterile field feet that are used. Alternatively, the foot pedal 160 may comprise two pedals, one for occlude and one for open. In an alternative foot pedal embodiment, the pedal 166 may operate a pneumatic line to cause a pressure activated valve or a cuff to occlude and open the vacuum line 136, for example, by forcing the actuator head 178 to move. In another alternative embodiment, the pedal 166 may turn, slide, or otherwise move a mechanical element, such as a flexible pull cable or push rod that is coupled to the actuator 176, to move the actuator head 178. The cable 168 may be supplied sterile and connected to the base 164 prior to a procedure. The occlusion and opening of the vacuum line 136 thus acts as an on and off switch for the pump 101 (via the pressure sensor 144). The on/off function may thus be performed by a user whose hands can focus on manipulating sterile catheters, guidewires, and accessories, and whose foot can turn the pump on and off in a non-sterile environment. This allows a single user to control the entire operation or the majority of operation of the system 100 for aspirating thrombus. This can be an advantage both in terms of a rapid, synchronized procedure, but is also helpful in laboratories where additional assistants are not available. The actuator 176 and anvil 180 may be controlled to compress the vacuum line 136 with a particular force, and the actuator 176 may be controlled to move at a particular speed, either when compressing or when removing compression. Speed and force control allows appropriate response time, but may also be able to add durability to the vacuum line 136, for example, by not over-compressing. The foot pedal 160 may communicate with the pinch valve 162 via a wired connection through the pump 101 or may communicate with the pinch valve 162 wirelessly. Additionally, or alternatively, the pump may be controlled by buttons 184.

It should be noted that in certain embodiments, the pinch valve 162 and the foot pedal 160 may be incorporated for on/off operation of the pinch valve 162 on the vacuum line 136, without utilizing the pressure sensor 144. In fact, in some embodiments, the pressure sensor 144 may even be absent from the system 100 for aspirating thrombus, the foot pedal 160 being used as a predominant control means.

Figure 2:
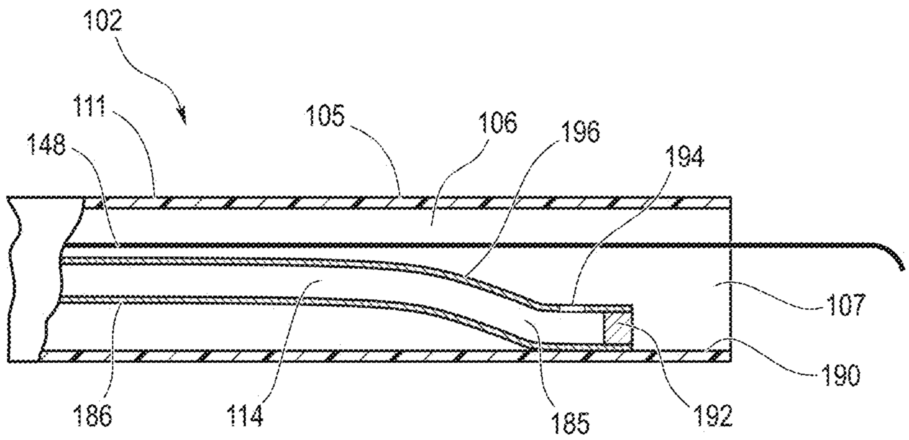
FIG. 2 is a sectional view of an exemplary distal end of the aspiration catheter of the system for aspirating thrombus of FIG. 1 according to an implementation of the present disclosure.

Turning to FIG. 2, a supply tube 186, which contains the catheter supply lumen 114, freely and coaxially extends within the over-the-wire guidewire lumen/aspiration lumen 106. At least a distal end 185 of the supply tube 186 is secured to an interior wall 190 of the guidewire lumen/aspiration lumen 106 of the catheter shaft 111 by adhesive, epoxy, hot melt, thermal bonding, or other securement modalities. A plug 192 is secured within the catheter supply lumen 114 at the distal end 185 of the supply tube 186. The plug 192 blocks the exit of pressurized fluid, and thus the pressurized fluid is forced to exit through an orifice 194 in the wall 196 of the supply tube 186. The free, coaxial relationship between the supply tube 186 and the catheter shaft 111 along their respective lengths, allows for improved flexibility. In some embodiments, in which a stiffer proximal end of the aspiration catheter 102 is desired (e.g., for pushability or even torqueability), the supply tube 186 may be secured to the interior wall 190 of the guidewire lumen/aspiration lumen 106 of the catheter shaft 111 along a proximal portion of the aspiration catheter 102, but not along a distal portion. This may be appropriate if, for example, the proximal portion of the aspiration catheter 102 is not required to track through tortuous vasculature, but the distal portion is required to track through tortuous vasculature. The free, substantially unconnected, coaxial relationship between the supply tube 186 and the catheter shaft 111 along their respective lengths, may also be utilized to optimize flow through the guidewire lumen/aspiration lumen 106, as the supply tube 186 is capable of moving out of the way due to the forces of flow (e.g., of thrombus/saline) over its external surface, such that the remaining inner luminal space of the guidewire lumen/aspiration lumen 106 self-optimizes, moving toward the lowest energy condition (least fluid resistance) or toward the largest cross-sectional space condition (e.g., for accommodating and passing pieces of thrombus).

Figure 3:
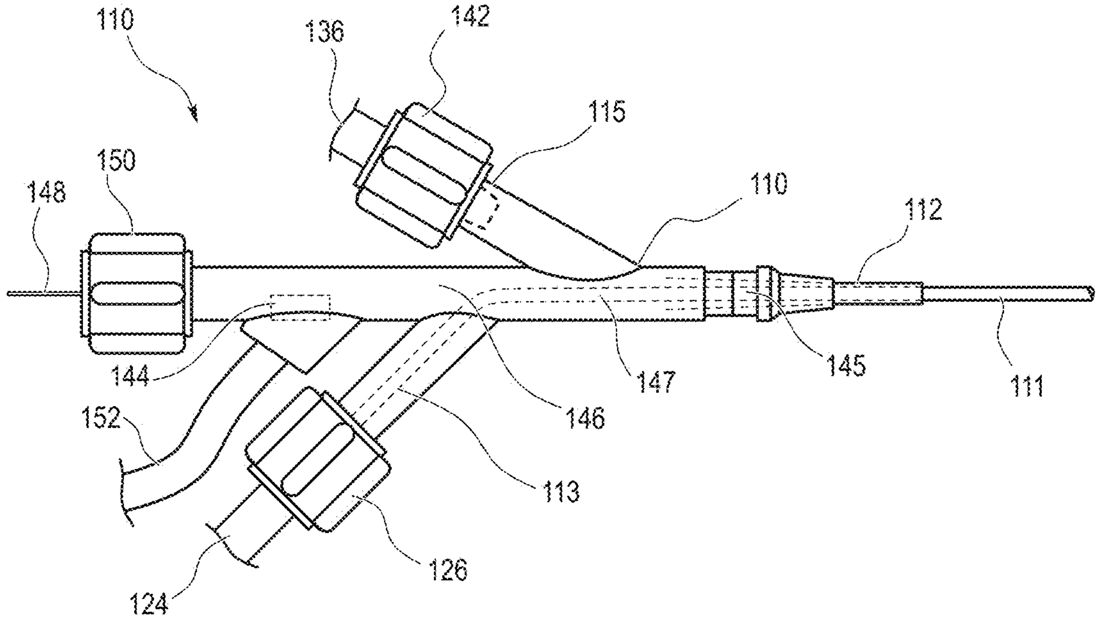
FIG. 3 is a detail view of an exemplary y-connector of the aspiration catheter of the system for aspirating thrombus of FIG. 1 according to an implementation of the present disclosure.
Figure 4:
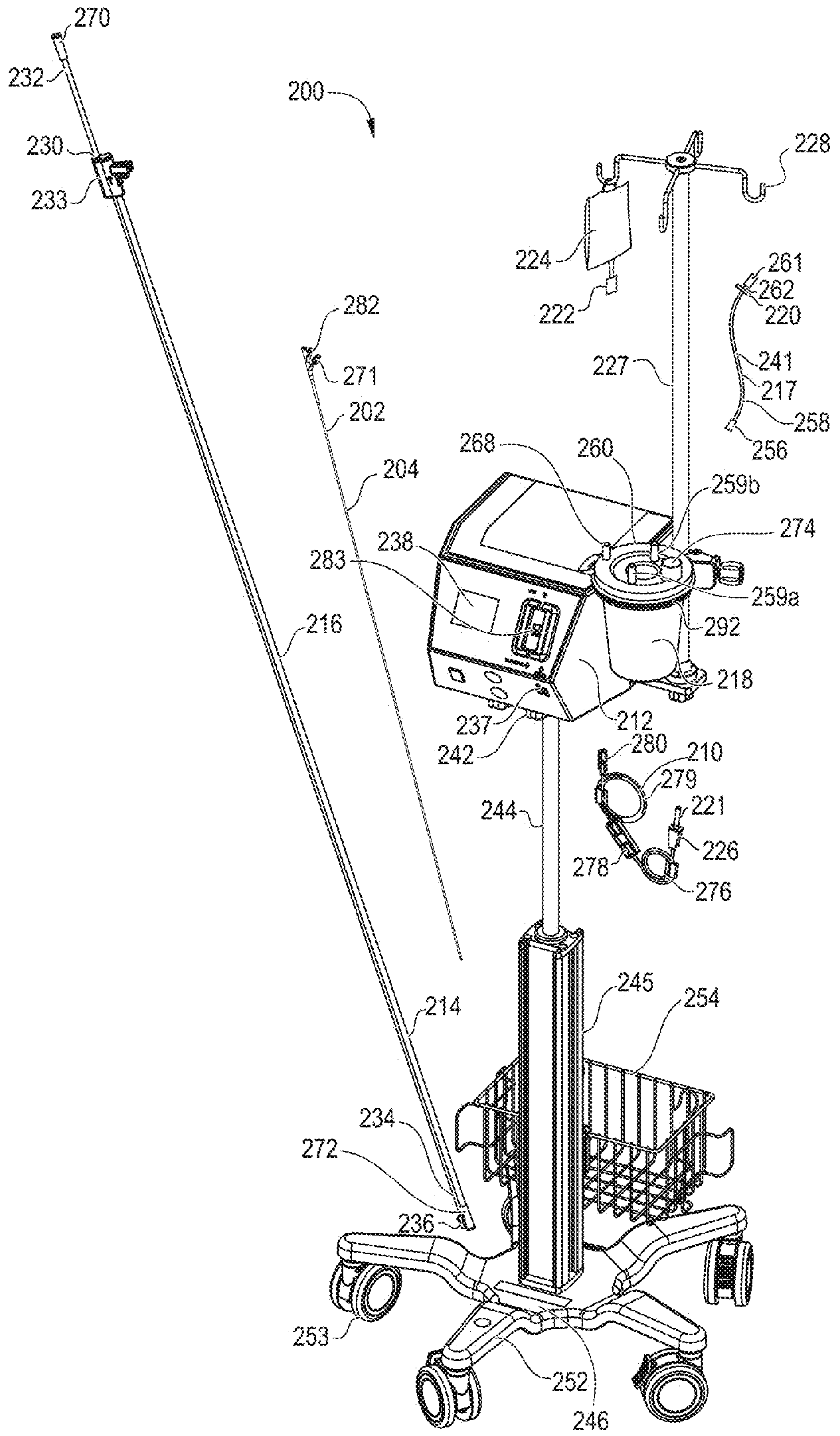
FIG. 4 is a plan view of exemplary disposable components of a system for aspirating thrombus according to an implementation of the present disclosure.
Figure 5:
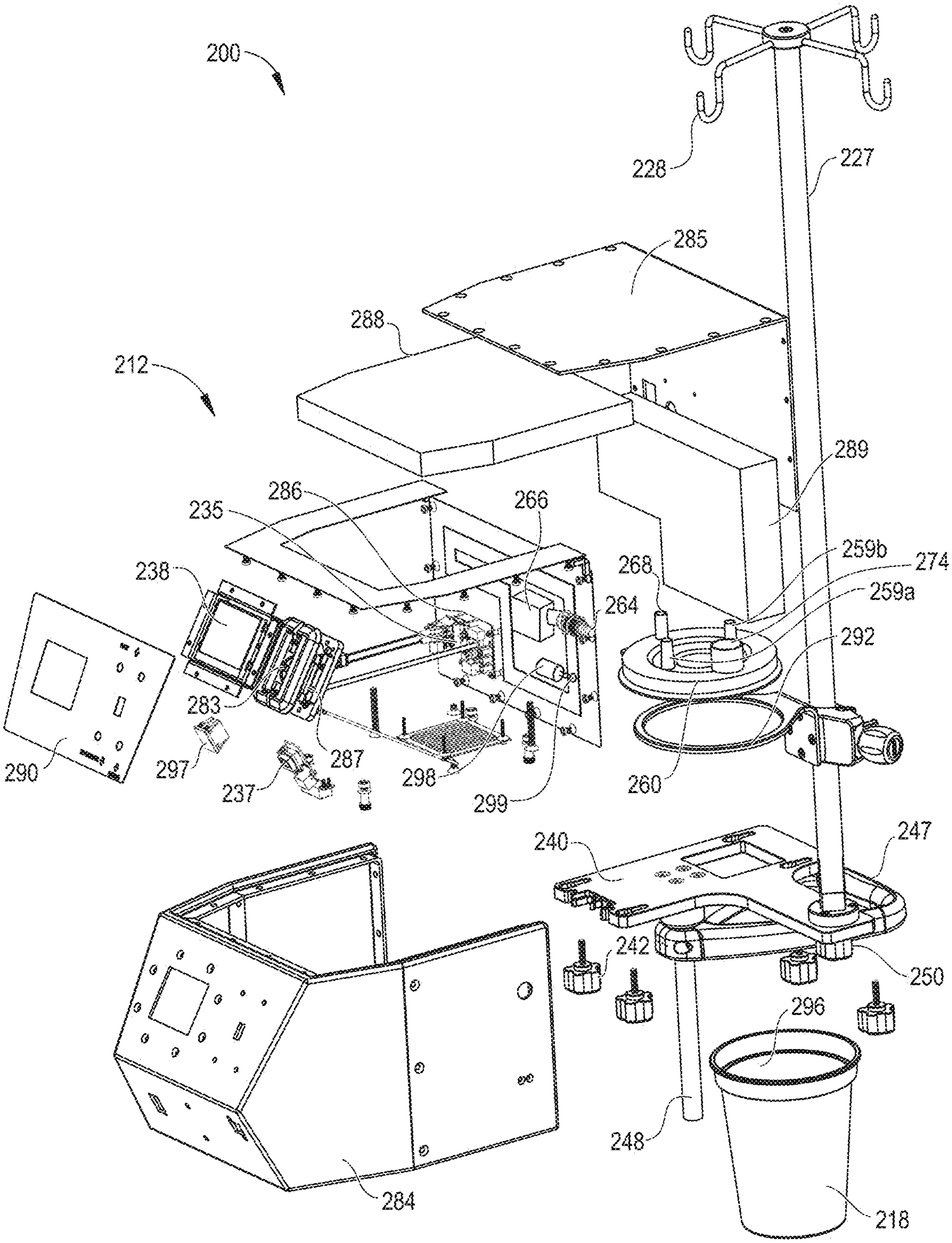
FIG. 5 is a perspective view of an exemplary system for aspirating thrombus of FIG. 3 according to an implementation of the present disclosure.

A system 200 for aspirating thrombus is illustrated in FIGS. 4-5. The system 200 for aspirating thrombus is similar to the system 100 and so the disclosure related to the system 100 is also applicable to the description of system 200. An aspiration catheter 202 is similar to the aspiration catheter 102 of FIGS. 1-3 and as such the description related to the aspiration catheter 102 of FIGS. 1-3 is also applicable to the description of the aspiration catheter 202.

The aspiration catheter 202 is configured for aspirating thrombus from peripheral vessels, but may also be configured with a size for treating coronary, cerebral, pulmonary or other arteries, or veins. The aspiration catheter 202/system 200 may be used in interventional procedures, but may also be used in surgical procedures. The aspiration catheter 202/system 200 may be used in vascular procedures, or non-vascular procedures (other body lumens, ducts, or cavities). The catheter 202 comprises an elongate shaft 204 configured for placement within a blood vessel of a subject; a catheter supply lumen 114 (FIG. 3) and a guidewire/aspiration lumen 106, each extending along the shaft, the supply lumen 114 having a proximal end 147 and a distal end 185, and the aspiration lumen 106 having a proximal end 145 (FIG. 3) and an open distal end 107 (FIG. 2); and an orifice or opening 194 at or near the distal end 185 of the supply lumen 114, the opening configured to allow the injection of pressurized fluid into the aspiration lumen 106 at or near the distal end 107 of the aspiration lumen 106 when the pressurized fluid is pumped through the supply lumen 114. In some embodiments, the orifice or opening 194 may be located proximal to the distal end 185 of the supply lumen 114. In some embodiments, the distal end 185 of the supply lumen 114 may comprise a plug 192. A pump set 210 (e.g., tubing set) is configured to hydraulically couple the supply lumen 114 to a pump within a saline drive unit (SDU) 212, for injecting pressurized fluid (e.g., saline, heparinized saline) through the supply lumen 114. Suction tubing 214, comprising sterile suction tubing 216 and non-sterile suction tubing 217, is configured to hydraulically couple a vacuum canister 218 to the aspiration lumen 106. A filter 220 may be carried in-line on the suction tubing 214, for example, connected between the sterile suction tubing 216 and the non-sterile suction tubing 217, or on the non-sterile suction tubing 217. The filter 220 is configured to capture large elements such as large pieces of thrombus or emboli.

The pump set 210 includes a saline spike 221 for connection to a port 222 of a saline bag 224, and an inline drip chamber 226 for visually assessing the movement of saline, as well as keeping air out of the fluid being injected. The saline bag 224 may be hung on an IV pole 227 on one or more hooks 228. A pressure sensor 230 such as a vacuum sensor may be used within any lumen of the pump set 210, the suction tubing 214, the supply lumen 114 or aspiration lumen 106 of the catheter 202, or any other component which may see fluid flow. The pressure sensor 230 is shown in FIG. 4 within a lumen at a junction between a first aspiration tube 232 and a handpiece 233. A cable 234 carries signals output from the pressure sensor 230 to a controller 235 (FIG. 5) in the SDU 212. A connector 236, electrically connected to the cable 234, is configured to be detachably coupled to a mating receptacle 237 (e.g., input jack) in the SDU 212. The SDU 212 also may have a display 238, including an LCD screen or alternative screen or monitor, in order to visually monitor parameters and status of a procedure. In alternative embodiments, the pressure sensor 230 may be replaced by another type of sensor that is configured to characterize fluid flow. In some embodiments, the sensor is a flow sensor, such as a Doppler flow velocity sensor.

The SDU 212 is held on a mount 240 by four locking knobs 242. The mount 240 is secured to a telescoping rod 244 that is adjustable from a cart base 245 via a cart height adjustment knob or other element 246. The mount 240 and a handle 247 are secured to the rod 244 via an inner post 248 that is insertable and securable within an inner cavity in the rod 244. The IV pole 227 secures to the mount 240 via a connector 250. The base 245 may include legs 252 having wheels 253 (e.g., three or more wheels or four or more wheels) and may be movable via the handle 247. The system 200 may also carry a basket 254 for placement of components, products, documentation, or other items.

In use, a user connects a first connector 256 at a first end 258 of the non-sterile suction tubing 217 to a second port 259 on the lid 260 of the canister 218, and connects a second connector 261 at a second end 262 of the non-sterile suction tubing 217 to a vacuum pump input 264 in the SDU 212. A vacuum pump 266 may be carried within the SDU 212 in order to maintain a vacuum/negative pressure within the canister 218. Alternatively, the vacuum inside the canister 218 may be maintained manually, without a vacuum pump, by evacuating the canister 218 via one or more additional ports 268. A user connects a first connector 270 of the sterile suction tubing 216 to an aspiration luer 271 of the aspiration catheter 202 (similar to luer 115) and connects the second connector 272 of the sterile suction tubing 216 to port 259*a* in the lid 260 of the canister 218. Connector 236 is then coupled to the mating receptacle 237 in the SDU 212 for communication with the handpiece 233 and/or the pressure sensor 230. For instance, the connector 236 can be snapped into mating receptacle 237 in the SDU 212 for communication with elements of the handpiece 233 and/or for communication with the pressure sensor 230, either via cable 234, and/or additional cables or wires. Alternatively, the connector 236 may couple to the mating receptacle 237 by clipping, friction fitting, vacuum fitting, or other means.

After allowing saline to purge through the supply tube 276, cassette 278, and injection tube 279 of the pump set 210, the user connects the luer connector 280 of the pump set 210 to a luer 282 of the aspiration catheter 202 (similar to luer 113). The cassette 278 (similar to cassette 121) is then attached to a saddle 283 in the SDU 212. The saddle 283 is configured to reciprocate a piston to inject the saline from the IV bag 224 at high pressure, after the cassette 278 is snapped in place, keeping the internal contents (e.g., saline) sterile. Systems configured for performing this type of sterile injection of high-pressure saline are described in U.S. Pat. No. 9,883,877, issued Feb. 6, 2018, and entitled, "Systems and Methods for Removal of Blood and Thrombotic Material", which is incorporated by reference in its entirety for all purposes. The SDU 212 is enclosed within a case 284 and a case lid 285. The controller 235 (FIG. 5) may reside on a circuit board 286. Noise from a motor 287 controlling the saddle 283 and from the vacuum pump 266 is abated by internal foam sections 288, 289. The saddle 283 may be moved directly by the motor 287, or may be moved with pneumatics, using a cycled pressurization. An interface panel 290 provides one or more switches 297 and the display 238. Alternatively, the cassette 278 may couple to the saddle 283 by clipping, friction fitting, vacuum fitting, or other means.

FIG. 5 illustrates aspects pertaining to the vacuum canister 218, in which aspirant (e.g., thrombus, blood, saline) that is evacuated from the patient through the aspiration lumen 106 is collected. The canister 218 may be held in a canister mount 292 carried by the IV pole 227, or alternatively carried by any other part of the system 200. A lid 260 is configured to cover a portion of the canister 218, such as in a snapping manner, to close an interior 296 of the canister 218. Alternatively, the lid 260 may couple to the canister 218 by screwing, clipping, friction fitting, or other means.

The lid 260 may comprise two or more ports, including the first port 259*a* and second port 259*b* for providing negative pressure/vacuum to the aspiration lumen 106. For example, the lid 260 may comprise two ports, three ports, four ports, or more than four ports. Sterile suction tubing 216 may be connected to the lid 260 of the vacuum canister 218 at a first port 274 for transmitting a negative pressure to the sterile suction tubing 216 and to the aspiration lumen 106 of the aspiration catheter 102. Non-sterile suction tubing 217 may be connected to the lid 260 of the vacuum canister 218 at a second port 259 for providing a negative pressure to the vacuum canister 218. A negative pressure may be provided to the non-sterile suction tubing 217 (and to sterile suction tubing 216 and the aspiration lumen 106 connected therewith) by a vacuum source (e.g., a vacuum pump or syringe). The system 200 may also comprise means for sealing the two or more ports of the lid 260 when not in use, such as one or more port caps. A filter may be placed over an entry to the second port 259 so as to prevent aspirant from traveling along the non-sterile suction tubing 217 from the vacuum canister 218 to the vacuum source.

The vacuum canister 218 preferably has a sufficient volumetric capacity for receiving all aspirant collected during the surgical procedure. Receptacles having a volumetric capacity of approximately 100 cubic inches, or receptacles having a diameter of approximately 5.0 inches and a height of approximately 7.0 inches, have been found to provide sufficient volumetric capacity.

Returning to FIG. 5, a solenoid 298 is carried internally in the SDU 212, and is configured to interface with the interior 296 of the canister 218, via the suction tubing 214, or via any additional tubing. The solenoid 298 is configured to vent the negative pressure inside the canister 218, by opening a valve 299 coupled to the solenoid (mechanically or electromagnetically) that opens the interior 296 of the canister 218 to ambient pressure. The venting allows any foaming of blood or fluid, such as any aspirated liquid, within the canister 218 to be reduced. Foaming can occur during a thrombolysis procedure due to cavitation, as air bubbles are formed. The solenoid 298 is then configured to close the valve 299, to allow negative pressure to again be built up within the interior 296 of the canister 218. The controller 235 is configured to automatically energize the solenoid 298, in order to allow for the degassing/defoaming. For example, the controller 235 may send a signal to energize the solenoid 298 based on the measurement of a targeted negative pressure and/or a targeted time of aspiration cycle. In other cases, the controller 235 can send a signal to energize the solenoid 298 every minute, every five minutes, every ten minutes, etc. Additionally, a user can operate the controller 235, and more generally the controller 174, of the system 200 through the interface panel 290 to initiate degassing/defoaming of the interior 296. The venting may also be able to remove air bubbles inside the other lumens of the catheter and tubing sets.

In some embodiments, the controller 235 can output or send a signal to energize the solenoid 298 to open the valve 299, in order to stop any aspiration, while still allowing the SDU 212 to deliver saline, medication, or saline combined with medication (e.g., thrombolytic drugs), so that the fluids can be delivered out of the open distal end 107 (instead of being aspirated through the aspiration lumen 106).

Figure 6:
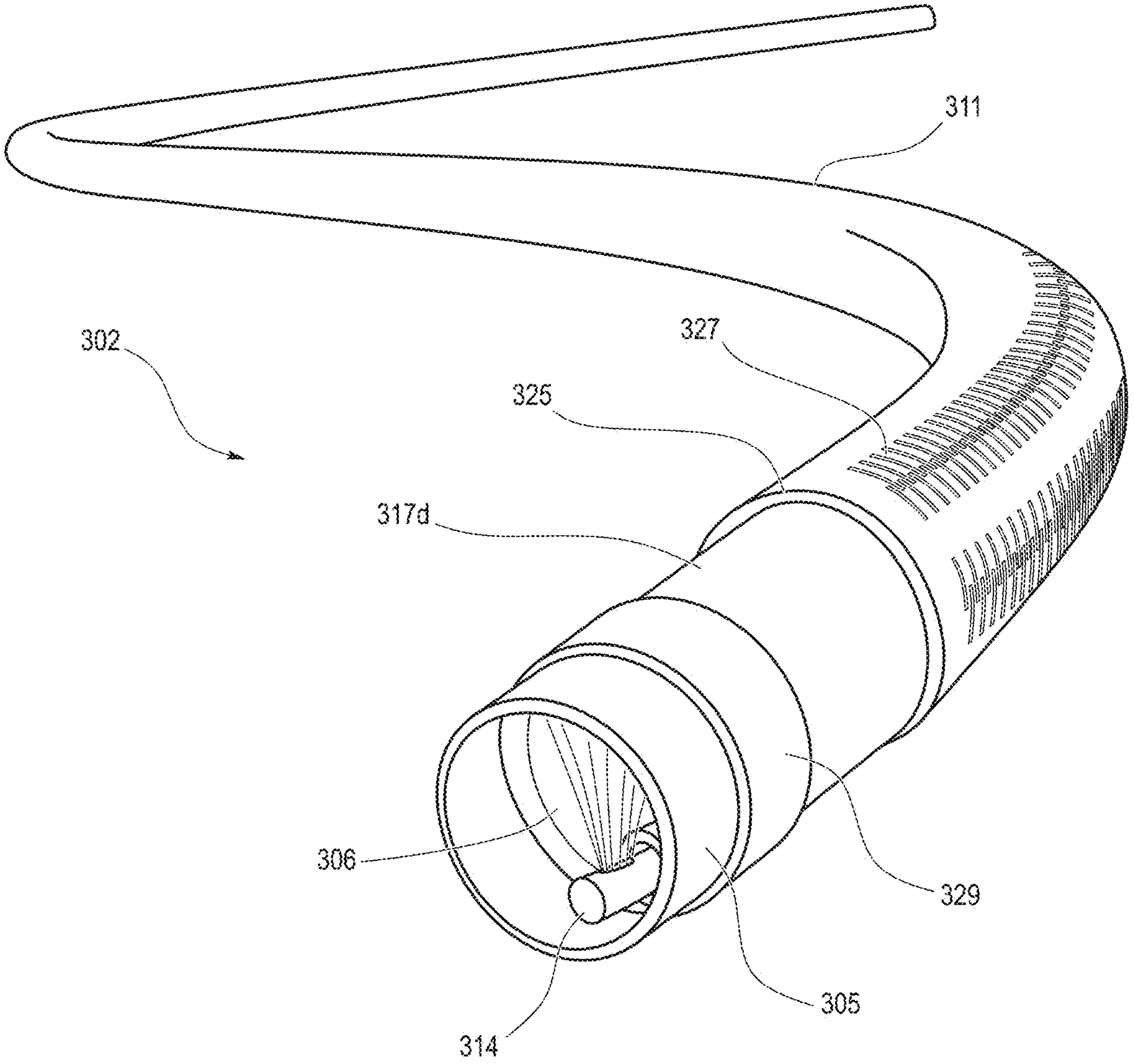
FIG. 6 is a perspective view of an exemplary aspiration catheter according to an implementation of the present disclosure.
Figure 7:
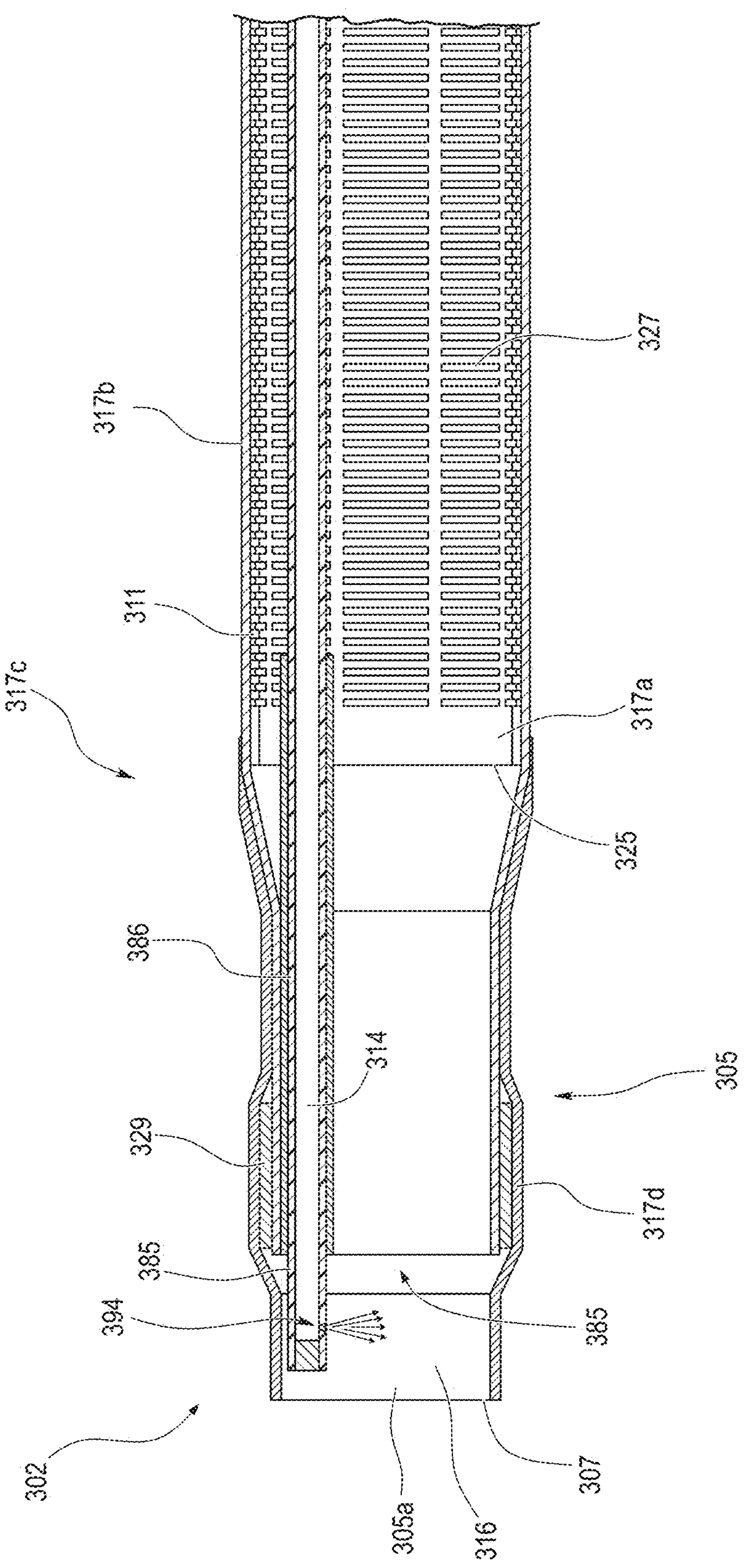
FIG. 7 is a sectional view of an exemplary aspiration catheter according to an implementation of the present disclosure.
Figure 8:
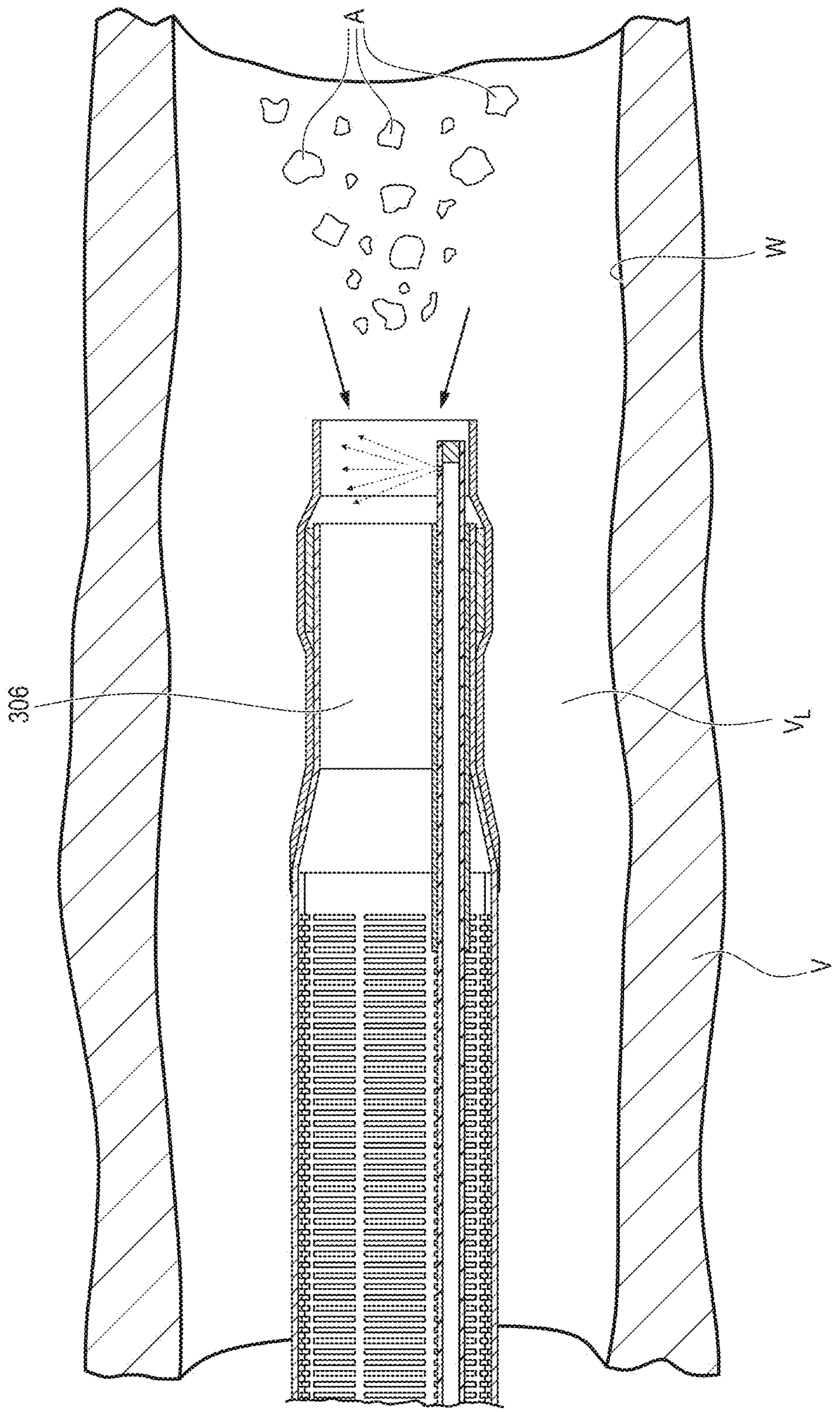
FIG. 8 illustrates the exemplary aspiration catheter within a body lumen aspirating thrombus according to an implementation of the present disclosure.

Turning to FIGS. 6-8, illustrated is another configuration of an aspiration catheter 302 that can be used with the systems 100 or 200 for aspirating thrombus. As such, the discussions related to the aspiration catheter 102 and the aspiration catheter 202 are also applicable to the aspiration catheter 302 illustrated in FIGS. 6-8.

As shown in more detail in FIGS. 6-8, aspiration catheter 302 includes an aspiration lumen 306 formed by a shaft 311, such as a hypotube, jacketed by a polymer jacket (or a polymer jacket is laminated on the hypotube). For instance, a shaft body 317*a* (shown in FIG. 7) is illustrated being jacketed by a jacket 317*b*. A distal end 305 of the aspiration catheter 302 includes a multilayer structure. A portion 317*c* of the jacket 317*b* extends distally of a distal end 325 of the shaft 311 to form part of the distal end 305. An outer layer or outer jacket 317*d* overlaps the jacket 317*b*, extends towards and overlaps a shaft distal end 325, and forms the aspiration catheter distal end 305*a*—i.e., the distal most end of the aspiration catheter with the distal opening 307. The outer jacket 317*d* protects a distal portion 385 of a supply tube 386 containing a supply lumen 314. While reference is made of a multilayer structure, it will be understood that one or more layers can be omitted or combined together. Additionally, one or more of the layers or shaft body can include braided or other members to increase strength and/or flexibility. Alternatively, the shaft and associated layers can be formed by extruding the shaft or using other structures to form the shaft. Alternatively, in other configurations, one or more supply lumens 314, and one or more supply tubes 386, can be associated with the shaft 311.

The supply lumen 314 may be configured to provide a high pressure fluid injection, such as saline, within the aspiration lumen 306 for macerating a thrombus as it is aspirated, such as illustrated in FIG. 8, where the aspiration catheter 302 is disposed within a vessel lumen (VL) of a vessel (V) and aspirant (A) is being drawing into the aspiration lumen 306. The saline injection may occur through orifice 394 near the distal end of the supply lumen 314 if the opening of the supply lumen is plugged with a plug similar to plug 192 (FIG. 2). Aspiration catheter 302 may also include a radiopaque (RO) ring 329 at or near the distal end 305 of aspiration catheter 302 for identifying the location of aspiration. The radiopaque ring 329 optionally encircles the aspiration catheter 302. In the illustrated configuration, the RO ring 329 is disposed between the jacket 317*b* and outer jacket 317*d*. The RO ring 329 can be formed of any suitable radiopaque material, such as tantalum, tungsten, platinum/iridium, gold, silver, and combinations or modifications thereof.

The radiopaque ring 329 also aids with reducing the likelihood of the distal end 305 collapsing during movement through the circulatory vessels where the distal end 305 can encounter vascular tortuosity. With the outer jacket 317*d* extending to the distal opening 307, flexibility of the distal end 305 is maintained. The radiopaque ring 329 provides structure to keep the distal opening 307 open and prevent the outer jacket 317*d* and jacket 317*b* collapsing during jetting and/or aspiration.

The shaft 311 can include one or more openings 327 to increase a flexibility of shaft 311 to aid with advancement of the aspiration catheter 302 through the tortuous anatomy of a patient. While reference is made to a "hypotube," it will be understood that other tubular structures can be used for the shaft 311. Additionally, the shaft 311 can be formed from polymers, metals, alloys, braided structures, coiled structures, and combinations or modifications thereof. Furthermore, the jacket 317*b* and outer jacket 317*d* can be formed of a variety of polymers and copolymers, plastics, PEBAX®, HYTREL®, rubber, nylon, polyethylene, polyurethane, polyester, and combinations or modifications thereof.

As shown in FIG. 8, aspiration according to the method of the present invention involves drawing clot(s) and other thrombus material into the aspiration lumen 306 using suction. Once in the aspiration lumen 306, the aspirant (A) may encounter a high pressure fluid injection from supply lumen 314, which helps to eviscerate the clot and remove it from the vasculature. In some situations, during aspiration, damage to the vessel might occur because the vessel wall (W) is drawn into the aspiration lumen 306 and brought into contact with the pressurized fluid injection (e.g., a high pressure saline spray at, for example, 650 psi) from supply lumen 314. Therefore, a tissue encroachment prevention assembly may prevent aspiration catheter 302 from damaging the vessel during aspiration. The tissue encroachment prevention assembly can be selectively added to the distal end 305 of the aspiration catheter 302 or the distal end 305 can be modified or changed to accommodate the tissue encroachment prevention assembly.

Figure 9:
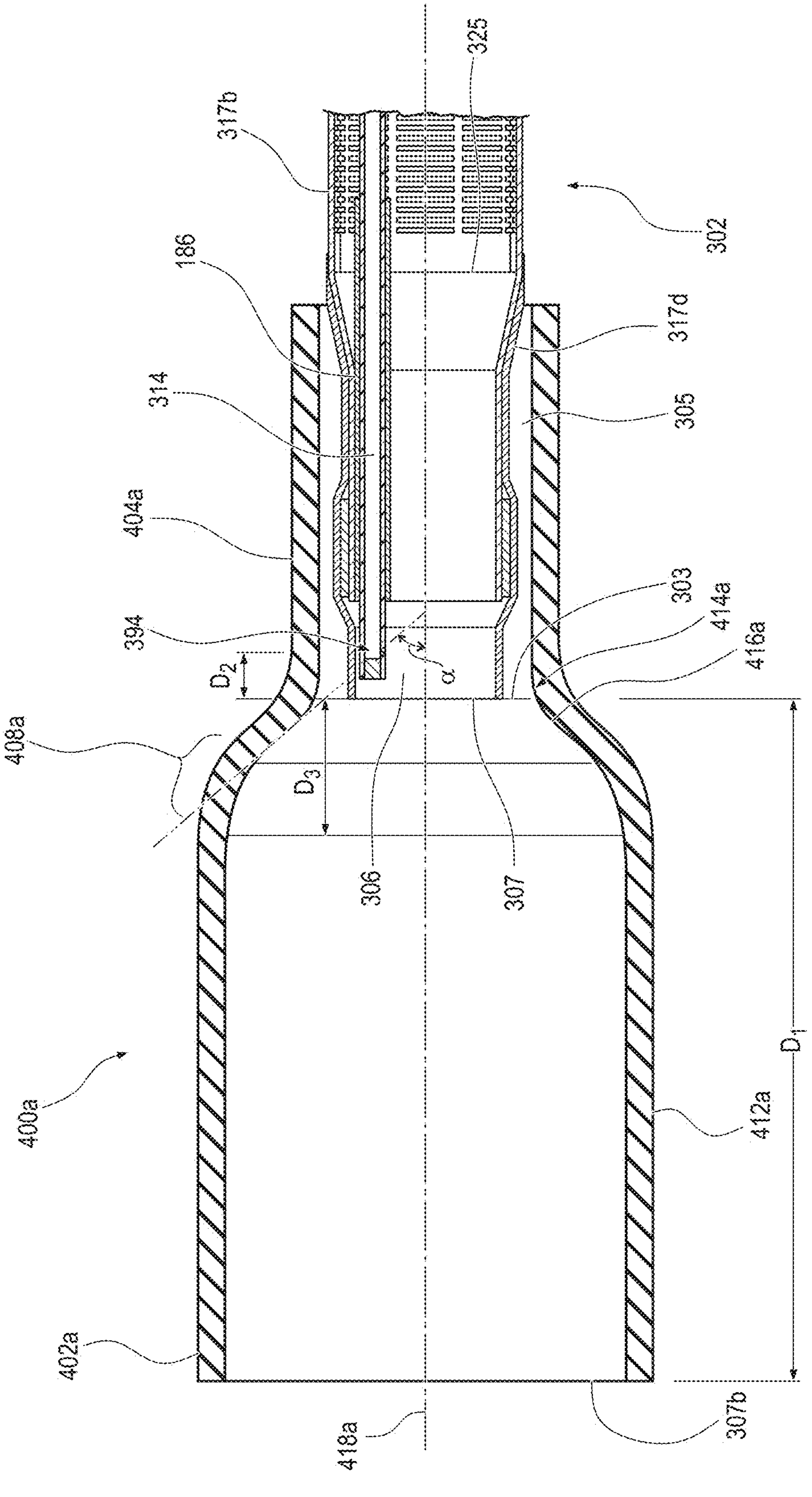
FIG. 9 is a sectional view of an exemplary aspiration catheter comprising a wide mouth tip according to an implementation of the present disclosure.

Turning to FIG. 9, illustrated is one configuration of a tissue encroachment prevention assembly that can be coupled, mounted, or otherwise affixed to the aspiration catheter 302, such as those illustrated in FIGS. 6 and 7. As illustrated, the location of the high pressure saline injection, such as at orifice 394 of supply lumen 314, may be far enough removed from the new distal opening 307*b* of the aspiration catheter 302 that if the vessel wall is partially drawn into the aspiration lumen 306, it will not come into contact with the high pressure saline spray from orifice 394 of supply lumen 314 and become damaged thereby.

Towards this end, aspiration catheter 302 can include a tissue encroachment prevention assembly 400*a*, as shown in FIG. 9, that repositions a distal end 307*b* of aspiration catheter 302 so that it is further removed from orifice 394 of supply lumen 314. The tissue encroachment prevention assembly 400*a* includes a tip body 402*a* configured to ensure that the vessel wall does not come into contact with the high pressure saline spray from supply lumen 314. FIG. 9 illustrates one embodiment of such a tip for aspiration catheter 302. As shown in FIG. 9, tip body 402*a* has a proximal end 404*a* and a distal end 406*a* having a wider diameter than the proximal end 404*a* to form a distal opening 307*b* that can function or forms a distal end of the aspiration catheter 302, i.e., the tissue encroachment prevention assembly 400*a* forms a wide-mouth tip, or wide-mouth distal end of an aspiration catheter, combined by aspiration catheter 302 and the tissue encroachment prevention assembly 400*a*. As such, reference to "aspiration catheter" can include the aspiration catheter 302 alone or the aspiration catheter 302 and a tissue encroachment prevention assembly in combination.

The proximal end 404*a* of tip body 402*a* can be glued or otherwise attached onto the distal end 305 of aspiration catheter 302 (such as to one or more of the outer jacket 317*d*, the jacket 317*b*, or other portion of shaft 311) through mechanical attachment, such as threads, keyed connections, quick release attachment, complementary fixing structures on the tip body 402*a* and a portion of the aspiration catheter (such as to one or more of the outer jacket 317*d*, the jacket 317*b*, or other portion of shaft 311), thermal bonding and combinations or modifications thereof, including combinations of adhesives, glues, cements, and mechanical attachment.

As mentioned above, the distal opening 307*b* is a new distal opening of the aspiration catheter that is spaced apart from distal opening 307 of aspiration catheter 302. Distal opening 307*b*, into which the vessel wall may be drawn during aspiration, is a further distance away from the location of the high pressure fluid injection, such as from orifice 394, than distal opening 307 of aspiration lumen 306. For example, the distal opening 307*b* may be a distance D1 away from distal opening 307, with D1 ranging from about 0.1 to about 1.0 inches. The orifice 394, or the high pressure fluid injection, may be a distance D2 away from distal opening 307, with D2 ranging from about 0.026 to about 0.060 inches, 0.01 inches to about 50 inches, or about greater than 0.035 inches, or is in a range between any two of the foregoing. The further setback for location of the high pressure fluid injection ensures that the vessel wall cannot be pulled far enough into aspiration catheter 302 to come into contact with the high pressure jet spray from supply lumen 314. The distance D1 can range from about 0.1 inches to about 0.2 inches, from about 0.2 inches to about 0.6 inches, from about 0.6 inches to about 1.0 inches, or is in a range between any two of the foregoing.

As mentioned before, the distal opening 307*b* may have a larger inner diameter than the inner diameter of distal opening 107 of aspiration catheter 102 or distal opening 307 of aspiration catheter 302. The larger diameter for distal end 307*b* of tip body 402*a* still allows a thrombus to be aspirated into the catheter and reach the high pressure saline spray—for example, at orifice 394—to be macerated. More generally, each of the distal end 305 of the aspiration catheter 302 and the distal end 412*a* of the tip body 402*a* can range from about 3 Fr. to about 26 Fr., with the distal end 412*a* of the tip body 402*a* being larger than the distal end 305 of the aspiration catheter. As such, each of the distal end 305 of the aspiration catheter 302 and the distal end 412*a* of the tip body 402*a* can be a diameter approximating a French size in a ranged between about 3 Fr and about 26 Fr, or any French size between 3 Fr and 26 Fr.

A ratio of the diameter of the distal opening 307*b* to the diameter of the distal opening 307 can range from about 1.25:1 to about 2:1, from about 2:1 to about 5:1, from about 5:1 to about 10:1, or is in a range between any two of the foregoing.

With continued reference to FIG. 9, an intermediate portion 408*a* transitions the tip body 402*a* from a proximal end 410*a* that selectively attaches to one or more of the outer jacket 317*d*, the jacket 317*b*, or other portion of shaft 311, and the distal end 412*a* having the distal opening 307*b*. The intermediate portion 408*a* can include a taper, conical configuration, square configuration, etc., or combinations or modifications thereof, with a transition proximal end 414*a* being generally aligned with a distal end 303 formed by the outer jacket 317*d* of the aspiration catheter 302. However, the transition proximal end 414*a* can be proximal or distal the distal end 303 of the outer jacket 317*d*. The angle of the transition from the distal end 412*a* to the proximal end 410*a* can aid with directing thrombus to the distal end 307 of aspiration catheter 302.

A distance D3 of the intermediate portion 408*a* can range from about 0.02 inches to about 0.1 inches, from about 0.1 inches to about 0.2 inches, from about 0.2 inches to about 0.5 inches, or is in a range between any two of the foregoing. An angle $\alpha$ between an inner wall 416*a* of the intermediate portion 408*a* and a longitudinal axis 418*a* of the tip body 402*a* can range from about 15 degrees to about 30 degrees, from about 30 degrees to about 45 degrees, from about 45 degrees to about 60 degrees, or is in a range between any two of the foregoing.

Tip body 402*a* may be made of polymer, such as a plastic, and glued onto the distal end 305 of aspiration catheter 302. Alternatively, tip body 402*a* may be made from PEBAX® (a block copolymer formed of a polyamide block and a polyether block) and heat-shaped over a mandrel to the desired configuration. The tip body 402*a* can then be reflowed/heat bonded onto the distal end 305 of aspiration catheter 302. In still another configuration, the tip body 402*a* can be formed of polycarb, nylon, polyurethane, or combinations or modifications thereof.

Turning to FIGS. 10A-11B, illustrated is another configuration of an aspiration catheter with a tissue encroachment prevention assembly. As with other tissue encroachment prevention assemblies, it provides means for preventing the aspiration catheter from damaging the vessel during aspiration. The disclosure related to the aspiration catheters and the tissue encroachment prevention assemblies described herein are also applicable to the tissue encroachment prevention assembly and the aspiration catheter of FIGS. 10A-10B.

Figure 11A:
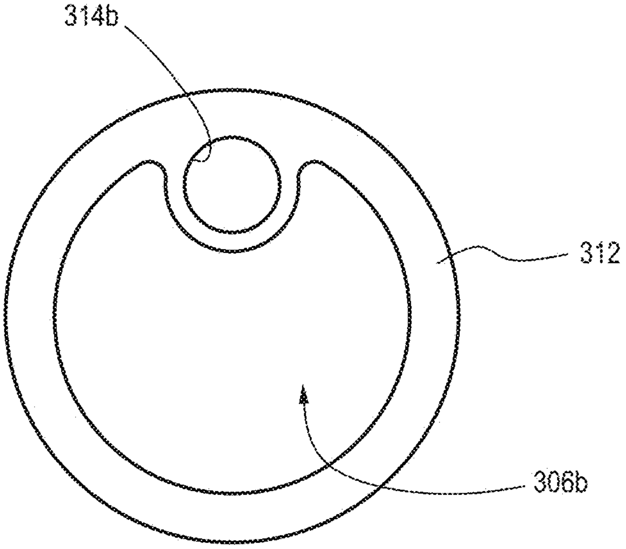
FIGS. 11A and 11B are cross-sectional views of exemplary dual-lumen catheter shafts in conjunction with a wide mouth tip according to an implementation of the present disclosure.
Figure 11B:
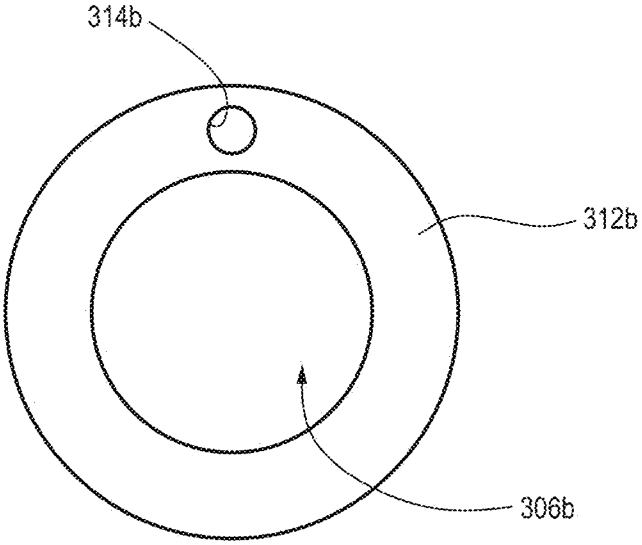

As illustrated in FIGS. 11A and 11B, an aspiration catheter 302*b* comprises a shaft 311*b* having a dual-lumen configuration with an aspiration lumen 306*b* that connects to or is in fluid communication with the vacuum source (e.g., vacuum pump 266 or syringe 130) and a supply tube lumen 314*b* that receives a supply tube 386*b* connected to or fluidly coupled to a high pressure fluid source (e.g., SDU 212) that delivers fluid to an orifice 394*b* for ejection or jetting fluid into the aspiration lumen 306*b*. The supply tube lumen 314*b* can be formed, such as through extrusion of the shaft 311*b*, in a wall 312*b* of the shaft 311*b*. As illustrated in FIG. 11A, the wall 312*b* protrudes inwardly to form the supply tube lumen 314*b*, such as extending inwardly about less than 25% of a diameter of the aspiration lumen 306*b*.

Alternatively, as illustrated in FIG. 11B, have a constant wall thickness so that the aspiration lumen 306*b* has a generally uniform cross-sectional diameter. The shaft 311*b*, and more generally, the aspiration catheter 302*b* can a diameter approximating a French size in a range between about 3 Fr and about 26 Fr, or any French size between 3 Fr and 26 Fr.

Returning to FIGS. 10A-10B, the tissue encroachment prevention assembly 400*b* also includes a tip body 402*b* forming a wide mouth tip. The tip body 402*b* has a similar form to tip body 402. However, since the aspiration catheter 302*b* has a shaft 311*b* formed as a multi-lumen shaft, such as an extruded polymer shaft 311*b*, the tissue encroachment prevention assembly 400*b* is coupled or mounted to the shaft 311*b* rather than to the outer jacket 317*d* and/or the jacket 317*b*, as described in relation to the tissue encroachment prevention assembly illustrated in FIGS. 7-8. For instance, the tissue encroachment prevention assembly 400*b* can be glued or otherwise attached onto the distal end 305*b* of aspiration catheter 302*b* through mechanical attachment, such as threads, keyed connections, quick release attachment, complementary fixing structures on the tip body 402*b* and a portion of the aspiration catheter, heat bonded and combinations or modifications thereof, including combinations of adhesives, glues, cements, and mechanical attachment.

Figure 12:
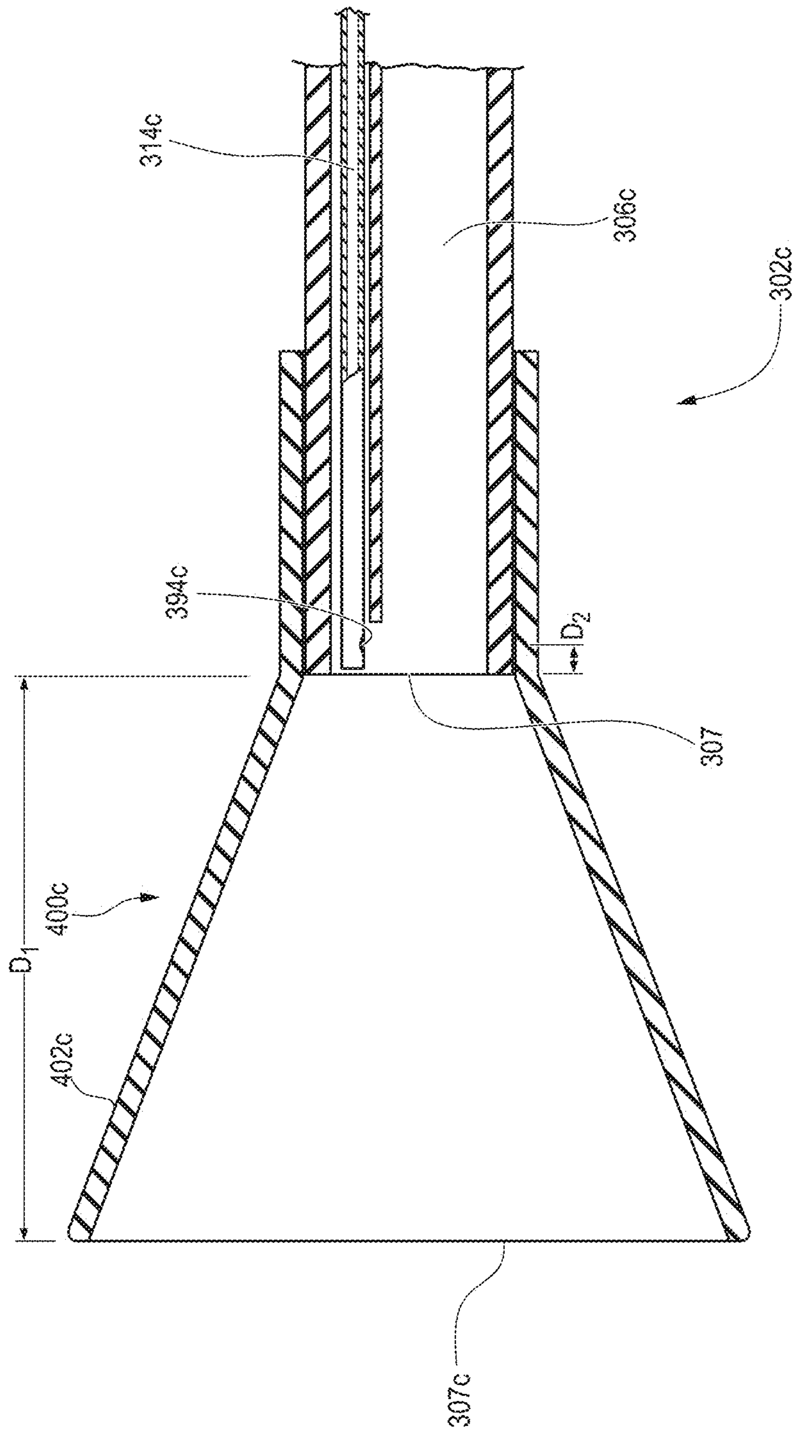
FIG. 12 is a sectional view of an exemplary aspiration catheter comprising a conical-shaped wide mouth tip according to an implementation of the present disclosure.

Turning to FIG. 12, illustrated is another configuration for an aspiration catheter with a tissue encroachment prevention assembly. As with the other tissue encroachment prevention assemblies described herein, it prevents the aspiration catheter from damaging the vessel during aspiration. The disclosure related to the aspiration catheters and the tissue encroachment prevention assemblies described herein are also applicable to the tissue encroachment prevention assembly and the aspiration catheter of FIG. 12.

FIG. 12 illustrates an embodiment for a wide mouth tip 400*c*, wherein the tip is conical in shape, rather than essentially cylindrical in shape, as in tips 400*a* and 400*b*. The tip 400*c* is illustrated as being mounted or otherwise coupled to aspiration catheter 302*c*, although tip 400*c* can be mounted to aspiration catheter 302 in a similar manner as tip 400*a* is mounted to aspiration catheter 302 (i.e., mounting or coupling of the tip 400*a* to one or more of the outer jacket 317*d*, the jacket 317*b*, or other portion of shaft 311).

In the illustrated configuration of FIG. 12, the inner diameter of distal opening 307*c* of tip body 402*c* may be wider than the inner diameter of the distal opening 307 of aspiration catheter 302 in FIGS. 7-8, for example. For instance, an inner diameter of the distal opening 307*c* can range from about 0.20 inches to about 0.75 inches. More generally, the distal end 307*c* of the tip body 402*c* can be sized to approximately the sizes referenced in relation to the distal end of tip body 402*a*.

The distal opening 307*c*, into which the vessel wall may be drawn during aspiration, is a further distance away from the location of the high pressure jet spray, such as from orifice 394*c*, than distal opening 307 of aspiration lumen 306*c*. For example, the distal opening 307*c* may be a distance D1 away from distal opening 307, the distance D1 being referenced in relation to tissue encroachment prevention assembly 400*a*). The orifice 394*c*, or the high pressure saline spray, may be a distance D2 away from distal opening 307 (such as the distance D2 being referenced in relation to tissue encroachment prevention assembly 400*a*). The further setback for location of the high pressure jet spray ensures that the vessel wall cannot be pulled far enough into aspiration catheter 302*c* to come into contact with the high pressure saline spray from orifice 394*c*.

Figure 13A:
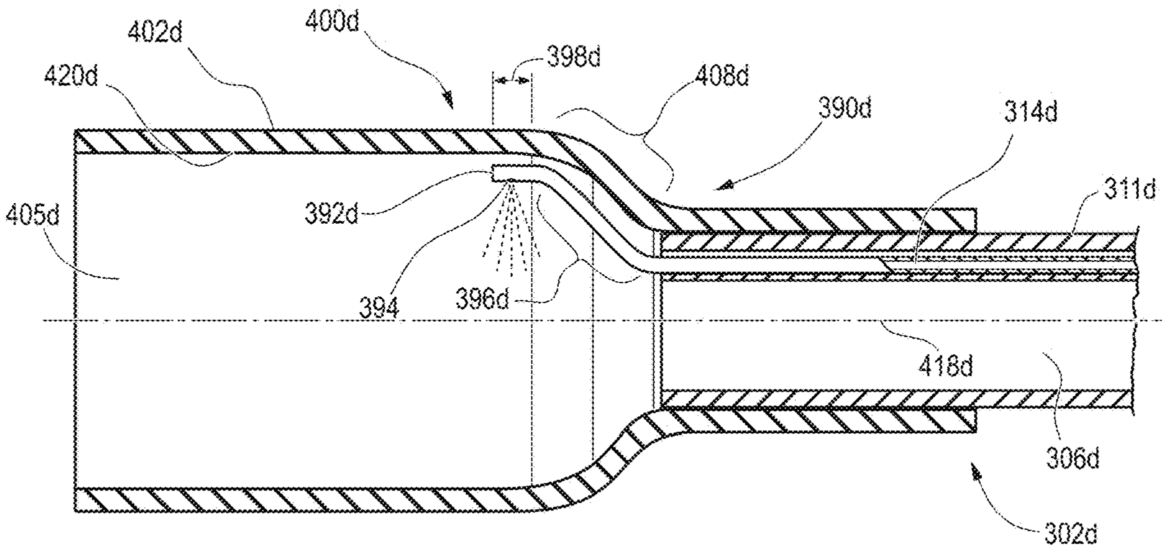
FIGS. 13A-13C are sectional views of exemplary aspiration catheters comprising a plurality of supply lumens according to an implementation of the present disclosure.
Figure 13B:
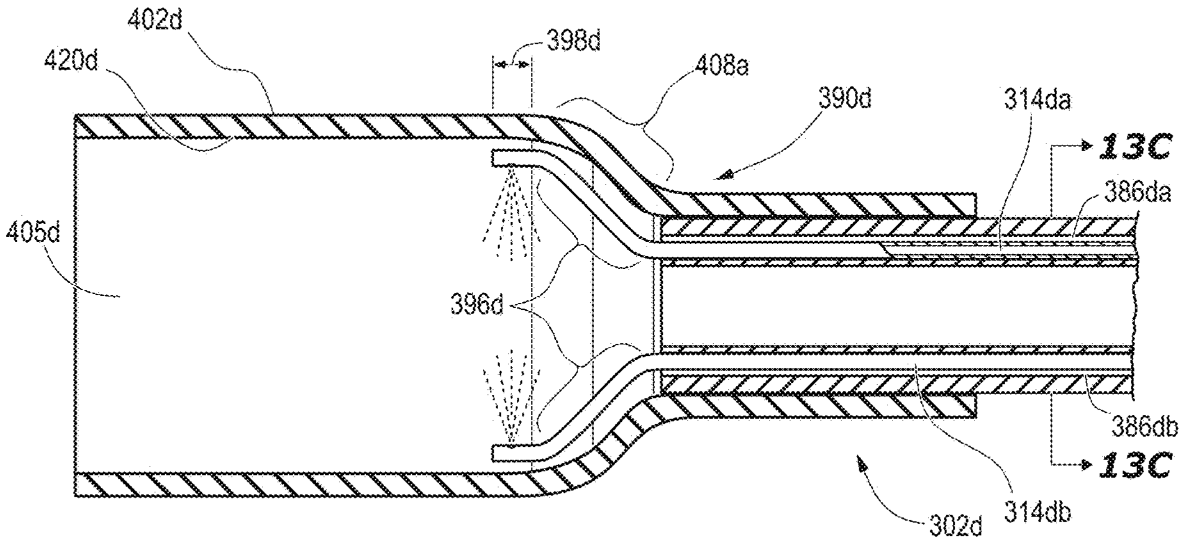
Figure 13C:
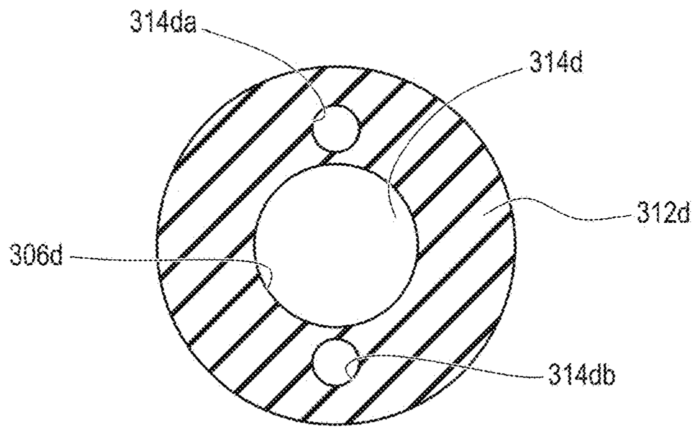

Turning to FIGS. 13A-13C, illustrated is another configuration of an aspiration catheter with a tissue encroachment prevention assembly. As with other tissue encroachment prevention assemblies, it is configured to prevent the aspiration catheter from damaging the vessel during aspiration. The disclosure related to the aspiration catheters and the tissue encroachment prevention assemblies described herein are also applicable to the tissue encroachment prevention assembly and the aspiration catheter of FIGS. 13A-13C.

Figure 10A:
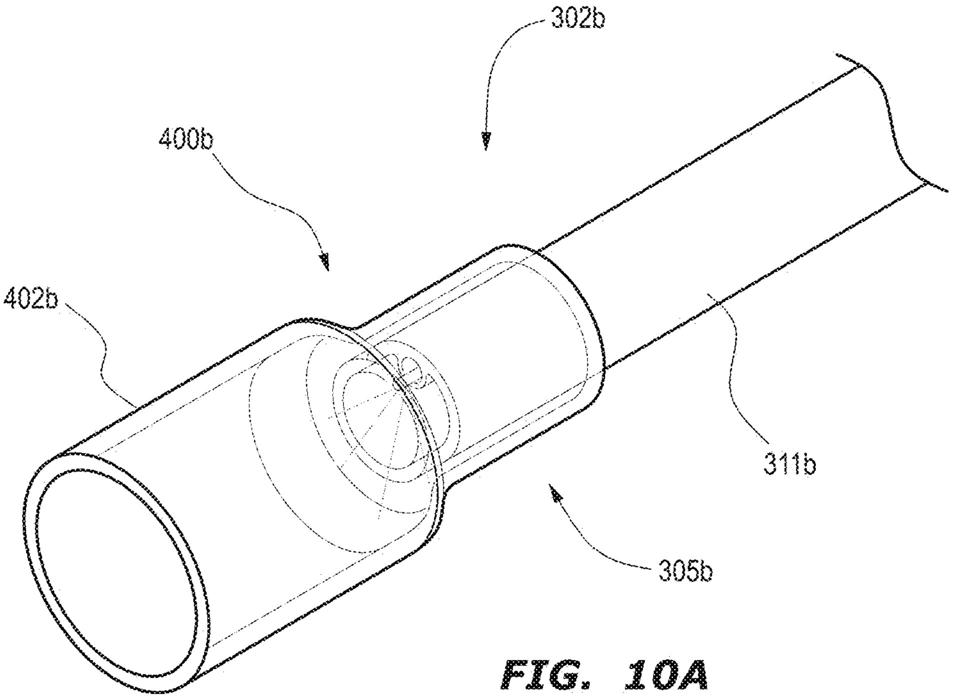
FIG. 10A is a perspective view of an exemplary aspiration catheter comprising a wide mouth tip according to an implementation of the present disclosure.
Figure 10B:
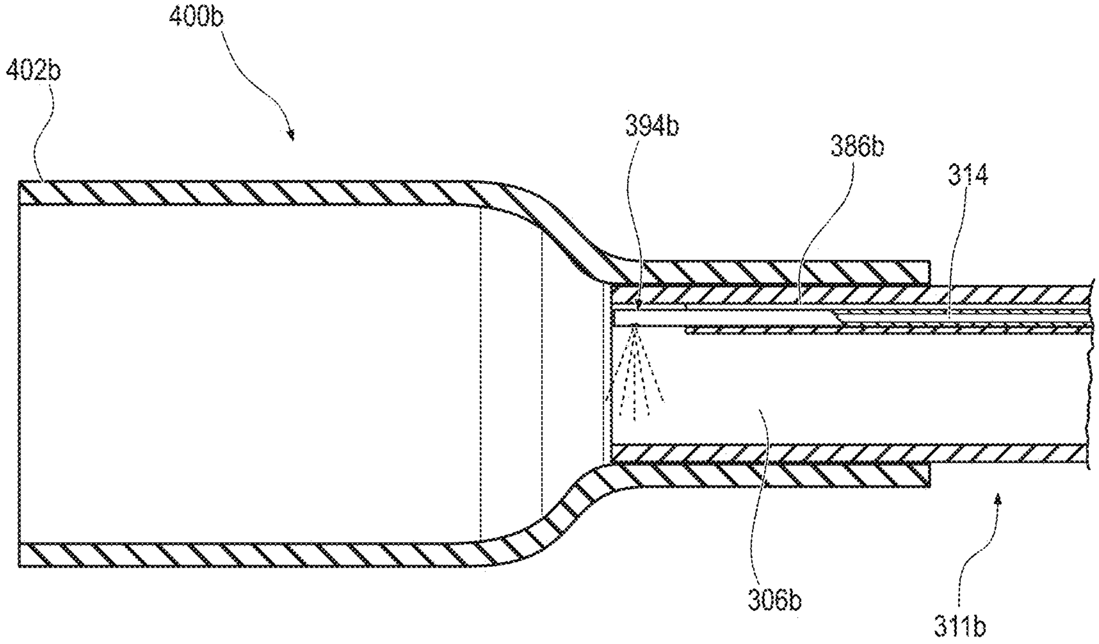
FIG. 10B is a cross-sectional view of the exemplary aspiration catheter of FIG. 10A according to an implementation of the present disclosure.

As illustrated in FIG. 13A, a tissue encroachment prevention assembly 400*d* is mounted to the aspiration catheter 302*d* in a similar manner to that illustrated in FIGS. 10A-10B. A supply tube 314*d* extends through the aspiration catheter 302*d* and, rather than being positioned so that the high pressure fluid injection from supply lumen 314*d* is directed into the aspiration lumen 306*d*, the supply tube 386*d* extends into a lumen 405*d* of the tip 400*d*. A distal region 390*d* of the supply tube 386*d* is angled so that a distal end 392*d* of the supply tube 386*d* is positioned in close proximity to an interior wall 420*d* of the tip 400*d* within the portion of the tip 400*d* having a wider or larger diameter. For instance, the distal region 390*d* includes an inclined portion 396*d* and a distal portion 398*d* extending from the inclined portion 396*d*. The inclined portion 396*d* is inclined, or at an angle, in relation to a longitudinal axis 418*d* of the tip 400*d* and can mirror or follow the inclination of the intermediate portion 408*d* or can have some other inclination different from the inclination of the intermediate portion 408*d*. The distal portion 398*d* extends generally parallel to the longitudinal axis 418*d* of the tip 400*d* but can alternatively be inclined away from or towards the longitudinal axis 418*d*—i.e., it can extend transversely to the longitudinal axis 418*d*.

In the configuration illustrated in FIG. 13A, the clot is macerated before it enters the (potentially) smaller-diameter aspiration lumen 306*d*. This helps with aspiration performance and helps to ease clogging. FIG. 13A shows an embodiment comprising one supply lumen 314*d* positioned within the wide mouth tip body 402*d*. Alternatively, as shown in FIG. 13B-13C, the tip body 402*d* may have multiple supply lumens, shown as supply lumens 314*da* and 314*db*, to facilitate maceration of the clot. Indeed, such an embodiment may comprise a plurality of supply lumens, for example two to eight supply lumens. While each supply tube 314*d* is illustrated as being similarly formed, i.e., having the inclined portion 396*d* inclined or at an angle in relation to a longitudinal axis 418*d* of the tip 400*d* and the distal portion 398*d* extending generally parallel to the longitudinal axis 418*d* of the tip 400*d*, it will be understood that the two or more supply tubes 386*d*, and associated supply lumens 314*d*, can be differently orientated. For instance, one or both of the supply tube 386*da* and the supply tube 386*db* can include distal portions 398*d* that can be orientated transversely to the longitudinal axis 418*d*. Similarly, one or both of the supply tube 386*da* and the supply tube 386*db* can include inclined portions 396*d* that inclined or at an angle in relation to the longitudinal axis 418*d*. More generally, each of the distal regions 398*d* can include at least one of (i) one or more portions that extend parallel to the longitudinal axis of the tip body 402*d*, and (ii) one or more portions that extend transversely to the longitudinal axis of the tip body 402*d*. By so doing, the clot is macerated before it enters the (potentially) smaller-diameter aspiration lumen. This helps with aspiration performance and helps to ease clogging.

As illustrated in FIG. 13C, an aspiration catheter 302*d* comprises a shaft 311*d* having a dual-lumen configuration with an aspiration lumen 306*d* that connects to, or is in fluid communication with, the vacuum source (e.g., vacuum pump 266 or syringe 130) and at least one supply tube lumen 314*d* that receives a supply tube 386*d* connected to or fluidly coupled to a high pressure fluid source (e.g., SDU 212) that delivers fluid to an orifice 394*d* for ejection or jetting fluid into the aspiration lumen 306*d*. The supply tube lumen 314*d* can be formed, such as through extrusion of the shaft 311*d*, in a wall 312*d* of the shaft 311*d*. As illustrated in FIG. 11*b*, the wall 312*d* may have a constant wall thickness so that the aspiration lumen 306*d* has a generally uniform cross-sectional diameter.

Although examples provided herein focus, in at least some respects, on an aspiration catheter that includes a single supply lumen and a single orifice 194, an aspiration catheter of a system (e.g., 100 or 200) can include any quantity of supply lumen and/or orifices through which fluid may pass to form any quantity of fluid jets. For example, a system for aspirating thrombus can include a quantity of supply lumens within a range of 1 to 10, or within a range of 2 to 8, or within a range of 3 to 6, and that are associated with a quantity of orifices (for forming fluid jets) within a range of 1 to 10, or within a range of 2 to 8, or within a range of 3 to 6. In some embodiments, the number of supply lumen and the number of orifices are proportional to one another. In other embodiments, each supply lumen may be associated with multiple orifices.

Furthermore, the Figures (see FIG. 2, for example) illustrates the orifice 194 is formed as a radial opening in the wall of the supply tube 186, with the orifice wall(s) that forms the orifice 194 between inner and outer surfaces of the supply tube 186 being perpendicular to the tangential axis of the wall 196. In some embodiments, an orifice for forming a fluid jet for an aspiration catheter of a system (e.g., 100 or 200) may be formed as an angled opening, where the orifice wall(s) that forms the orifice (between inner and outer surfaces of a material) has an acute or obtuse angle relative to the tangential axis of the material on which the orifice is formed (e.g., material of a supply tube or an additional component connected to the supply tube). For example, the angle between the orifice wall(s) and the tangential axis of the material on which the orifice is formed can be within a range of 20° to 70°, or 30° to 60°, or 40° to 50° (or within their complementary ranges).

The orifice(s) of an aspiration catheter of a system (e.g., 100 or 200) for providing fluid jets (i.e., "jet-forming" orifices) may be implemented with various sizes or shapes in different embodiments. In one example, an orifice may comprise a circular hole with a diameter between 0.03 mm (0.001 inches) and 0.15 mm (0.006 inches), or between about 0.0508 mm (0.002 inches) and about 0.1016 mm (0.004 inches), or about 0.0787 mm (0.0031 inches). The diameter of the supply lumen 114 may be between about 0.3048 mm (0.012 inches) and about 0.4826 mm (0.019 inches), or between about 0.3556 mm (0.014 inches and about 0.4318 mm (0.017 inches), or within any range having end points within any one or combination of the foregoing ranges. As another example, an orifice may comprise a rectangular hole with each side thereof having a length between 0.02 mm (0.0008 inches) and 0.20 mm (0.008 inches). In some implementations, the total cross-sectional area of all jet-forming orifices of an aspiration catheter of a system is between 0.002 mm^2 and 0.02 mm^2, or between 0.003 mm^2 and 0.015 mm^2, or between 0.005 mm^2 and 0.01 mm^2. In some embodiments, pressure measured at the deliver location of each jet-forming orifice during operation of the system (e.g., 100 or 200) is between 400 psi (2.6 MPa) and 2,000 psi (13.8 MPa), or between 500 psi (3.4 MPa) and 2,000 psi (13.8 MPa), or between 600 psi (4.1 MPa) and 1,750 psi (12.1 MPa).

FIGS. 9-13C generally illustrate tissue encroachment prevention assemblies that increase a diameter of the distal opening of the aspiration catheter as a whole, while moving a location of that distal opening away from the orifice, or the high pressure jet, to limit tissue damage to any tissue that might be drawn into the aspiration lumen during aspiration. While this is one approach to limiting tissue damage, or preventing tissue encroachment, other approaches are possible, including those illustrated in FIGS. 14A-18D. Generally, in these approaches, access to the aspiration lumen of the aspiration catheter is controlled or limited so that tissue does not encroach or be drawn into the aspiration lumen, while thrombus or aspirant is still capable of being collected. The disclosure related to the aspiration catheters and the tissue encroachment prevention assemblies described herein are also applicable to the tissue encroachment prevention assembly and the aspiration catheter of FIGS. 14A-18D.

Figure 14A:
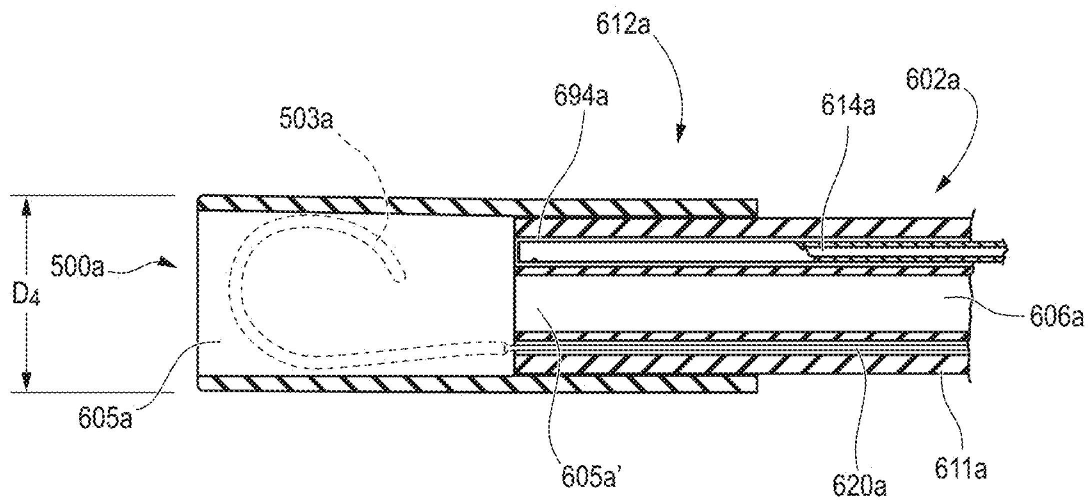
FIGS. 14A and 14B are sectional views of an exemplary aspiration catheter comprising an expandable member and a memory shape actuating member according to an implementation of the present disclosure.
Figure 14B:
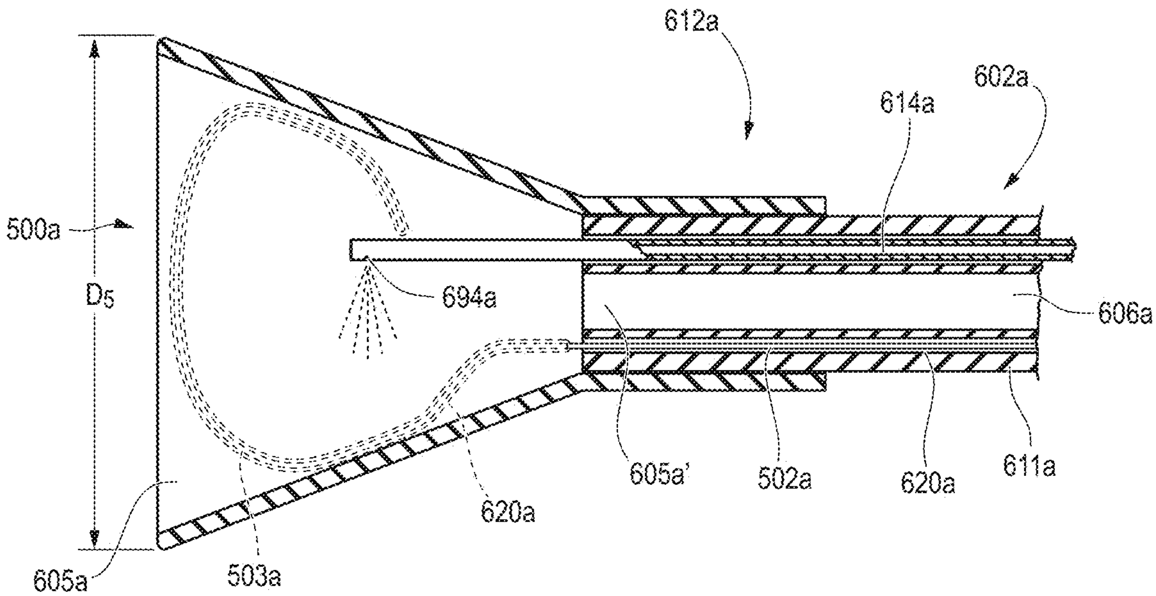

Turning to FIGS. 14A and 14B, illustrated is another embodiment for a tissue encroachment prevention assembly. The disclosure related to the aspiration catheters and the tissue encroachment prevention assemblies described herein are also applicable to the tissue encroachment prevention assembly and the aspiration catheter of 14A and 14B. As shown in FIGS. 14A and 14B, the tissue encroachment prevention assembly of catheter 602*a* may comprise an expandable member 500*a*, such as a cage, skirt, or basket that is configured to prevent vessel tissue from being drawn into the aspiration lumen 606*a* and coming into contact with the high pressure spray from supply lumen 614*a* during aspiration. The expandable member 500*a* may be made of nitinol, plastic, other polymer, and combinations or modifications thereof. The expandable member 500*a* may be positioned at or near the distal end 612*a* of aspiration catheter 602*a* in a native state, shown in FIG. 14A. In the embodiment of FIGS. 14A and 14B, the expandable member 500*a* is expanded by deployment of a memory shape member 502*a*, such as a NITINOL wire.

The memory shape member 502*a* may be housed in a housing lumen 620*a*, which is located inside aspiration lumen 606*a*. Towards this end, catheter 602*a* may comprise a hypotube extruded with three lumens—an aspiration lumen 606*a*, a supply tube lumen 614*a*, and a housing lumen 620*a*. The tubing may comprise braided reinforced PEBAX® with appropriate durometers to give desired flexibility and kink resistance. While the memory shape member 502*a*, such as a NITINOL wire, has been pre-shaped or preformed into a coil structure, it will exist in an uncoiled, straight form while in the housing lumen 620*a*. Upon its deployment from the housing lumen 620*a*, the memory shape member 502*a* will return to the preset shape, such as a coil, as shown in FIGS. 14A and 14B. As the memory shape member 502*a* expands into the preset shape, it will inflate the expandable member 500*a*, thereby increasing an inner diameter of distal opening 605*a*. In the expandable member's native state, distal opening 605*a* may have an inner diameter D4 of 0.05 inches to 0.35 inches (as shown in FIG. 14A). Upon transition to an expanded state the expandable member 500*a*, distal opening 605*a* may have a larger inner diameter D5 of 0.1 inches to 0.75 inches (as shown in FIG. 14B). Stated another way, the distal end of the aspiration catheter 602*a* can transition from a first state or native state having a first outside diameter to the enlarged state having a second outside diameter that is larger than the first outside diameter, where each of the first outside diameter and the second outside diameter can be selected from a French size in a range between about 3 Fr and about 26 Fr, or any French size between 3 Fr and 26 Fr.

To aid in deployment of the memory shape member 502*a* and its adoption of a preset configuration, expandable member 500*a* may optionally contain a channel 503*a* that mirrors the preset configuration of memory shape member 502*a*. In this way, channel 503*a* may delineate the path the memory shape member 502*a* will need to take upon deployment in order to adopt its preset configuration.

Expansion of expandable member 500*a* helps to prevent vessel damage during aspiration by relocating the distal opening 605*a* further from the supply tube lumen—and thus the high pressure fluid injection from orifice 694*a*—than would be the position of the distal opening 605*a*' at the distal end 612*a* of catheter 602*a* without expandable member 500*a*. Optionally, supply lumen 614*a* may extend beyond distal end 612*a* of catheter 602*a* into a lumen of expandable member 500*a*, as shown in FIG. 14B. Deployment of memory shape member 502*a* may still prevent vessel tissue from being drawn far enough into the expandable member 500*a* to encounter the high pressure fluid injection from supply lumen 614*a* so as to prevent vessel damage.

Figure 15A:
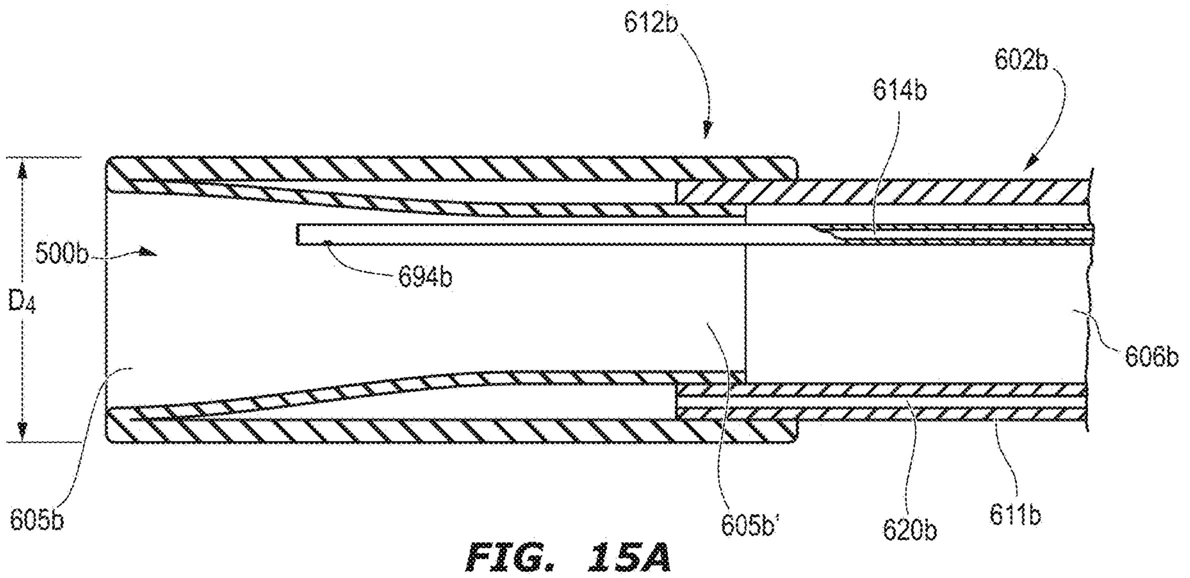
FIGS. 15A and 15B are sectional views of an exemplary aspiration catheter comprising an expandable member and a liquid infusion actuating member according to an implementation of the present disclosure.
Figure 15B:
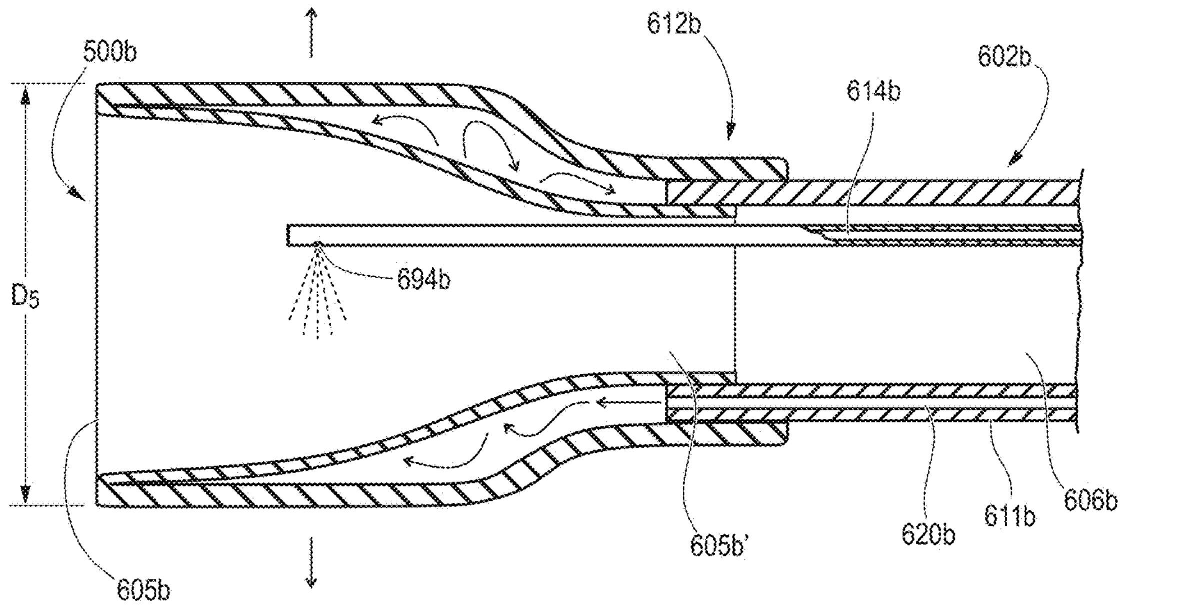

Turning to FIGS. 15A and 15B, illustrated is another embodiment for a tissue encroachment prevention assembly. The disclosure related to the aspiration catheters and the tissue encroachment prevention assemblies described herein are also applicable to the tissue encroachment prevention assembly and the aspiration catheter of FIGS. FIGS. 15A and 15B. As shown in FIGS. FIGS. 15A and 15B, the tissue encroachment prevention assembly of catheter 602*b* may comprise an expandable member 500*b*, such as an inflatable balloon, that is configured to prevent vessel tissue from being drawn into the aspiration lumen 606*b* and coming into contact with the high pressure spray from supply lumen 614*b* during aspiration. The expandable member 500*b*, such as an inflatable balloon, may be made of thermoplastic polyurethanes (TPUs), PET, Nylon, thermoplastic elastomers, other elastomers, and combinations or modifications thereof. The expandable member 500*b* may be positioned at or near the distal end 612*b* of aspiration catheter 602*b* in a native state, shown in FIG. 15A. In the embodiment of FIGS. 15*a* and 15*b*, the expandable member 500*b* is inflated using a fluid injection through second supply lumen 620*b*, such as a saline infusion. Upon infusion of fluid through the second supply lumen 620*b*, expandable member 500*b* inflates such that distal opening 605*b* has a larger inner diameter D5 than the inner diameter D4 (similar to aspiration catheter 602*a*) it had before inflation of the expandable member. Similar to aspiration catheter 602*a*, the distal end of the aspiration catheter 602*b* can transition from a first state or native state having a first outside diameter to the enlarged state having a second outside diameter that is larger than the first outside diameter, where each of the first outside diameter and the second outside diameter can be selected from range between about 3 Fr and about 26 Fr, or any French size between 3 Fr and 26 Fr.

Expansion of expandable member 500*b* helps to prevent vessel damage during aspiration by relocating the distal opening 605*b* further from the supply tube lumen—and thus the high pressure fluid injection from orifice 694*b*—than would be the position of the distal opening 605*b*' at the distal end 612*b* of catheter 602*b* without expandable member 500*b*. Optionally, supply lumen 614*b* may extend beyond distal end 612*b* of catheter 602*b* into the lumen of expandable member 500*b*, as shown in FIG. 15B. Expansion of expandable member 500*b* may still prevent vessel tissue from being drawn far enough into the expandable member 500*b* to encounter the high pressure fluid injection from supply lumen 614*b* so as to prevent vessel damage.

Figure 16A:
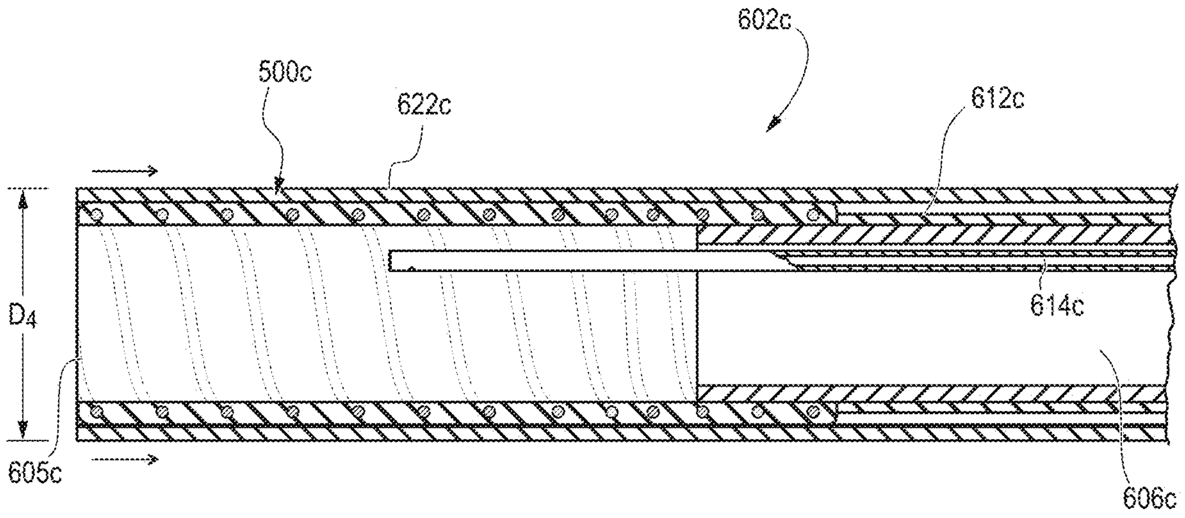
FIGS. 16A and 16B are sectional views of an exemplary aspiration catheter comprising an expandable member housed in an outer sheath according to an implementation of the present disclosure.
Figure 16B:
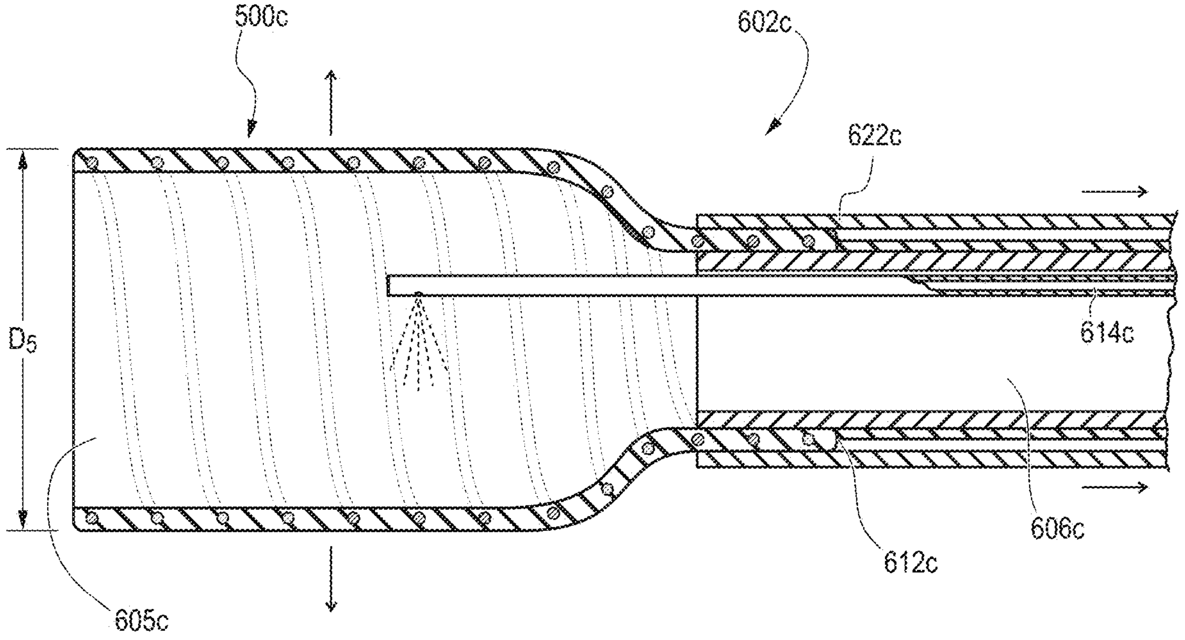

Turning to FIGS. 16A and 16B, illustrated is another embodiment for a tissue encroachment prevention assembly. The disclosure related to the aspiration catheters and the tissue encroachment prevention assemblies described herein are also applicable to the tissue encroachment prevention assembly and the aspiration catheter of 16A and 16B. As shown in 16A and 16B, the tissue encroachment prevention assembly of catheter 602*c* may comprise an expandable member such as a cage, skirt, or basket 500*c* that is configured to prevent vessel tissue from being drawn into the aspiration lumen 606*c* and coming into contact with the high pressure spray from supply lumen 614*c* (not shown, similar to all other supply lumens 314-614*b*) during aspiration. The expandable cage or basket may be made of NITINOL, plastic, other polymer, thermoplastic elastomers, other elastomers, and combinations or modifications thereof.

As shown in FIGS. 16A and 16B, the aspiration catheter 602*c*, including the expandable member 500*c*, may be housed in an outer sheath 622*c*. Upon retraction of the outer sheath 622*c*, the expandable member 500*c* is expanded over the distal tip 612*c* of catheter 602*c*. The expanded member 500*c* prevents the vessel wall from being drawn into the aspiration lumen 606*c* during aspiration. The outer sheath 622*c* may be exterior to the outer jacket 317*d* and/or jacket 317*b* (FIG. 9), or between the outer jacket 317*d* and jacket 317*b*, of catheter 602*c*. Alternatively, if catheter 602*c* is an extruded hypotube, the outer sheath 622*c* may be exterior to the catheter shaft 611*b* (shown in FIGS. 15A and 15B). The expandable cage or basket 500*c* is configured to enlarge the inner diameter of the distal opening 605*c* of catheter 602*c* from a first inner diameter D4 to a second, and larger, inner diameter D5 (the first inner diameter D4 and the second inner diameter D5 can be similarly sized to aspiration catheter 602*a*) For example, the first inner diameter D4 of distal opening 605*c* may be 0.05 inches to 0.35 inches, from about 0.079 inches to about 0.13 inches, or ranges between any two of the forgoing, and the inner diameter D5 of distal opening 605*c* may be 0.10 inches to 0.75 inches. Stated another way, the distal end of the aspiration catheter 602*c* can transition from a first state or native state having a first outside diameter to the enlarged state having a second outside diameter that is larger than the first outside diameter, where each of the first outside diameter and the second outside diameter can be selected from a range between about 3 Fr and about 26 Fr, or any French size between 3 Fr and 26 Fr.

In order to enlarge the inner diameter of distal opening 605*c* of catheter 602*c*, the member 500*c* is positioned at or distal the distal end 612*c* of catheter 602*c* after deployment from the outer sheath 622*c*. The expandable member 500*c* will still allow a clot to enter the aspiration lumen 606*c*, while preventing the vessel wall from entering the aspiration lumen 606*c*, during aspiration.

In the area of thrombectomy, a blood clot is removed from the body using a method of action. In the case of the present invention, the method of action is active aspiration. During active aspiration, the clot is ingested into an aspiration catheter and removed from the body by way of suction. As with any minimally invasive percutaneous intervention, the smaller the incision or access point into the body, the less likelihood there is of complications. In order to make the thrombectomy device smaller, yet still large enough to ingest a clot of any substance, a method of catheter expansion is needed. The invention disclosed herein is directed to such a method of expansion. In one embodiment, a thrombectomy device is constructed from a woven or braided material. Such material could be a plastic, a metal, or a plurality of materials.

A skilled artisan would understand that such a woven or braided material may be easily expanded with minimal force in an axial direction. In the present invention, there exist a number of ways to apply a linear force in the axial direction. Two embodiments will be discussed below.

In the first embodiment, shown in FIG. 17A-17B, catheter 702*a* comprises a woven or braided portion 732*a* at its distal end 712*a* and a hypotube portion 711*a*, such as that discussed with reference to FIGS. 9-13B, at its proximal end 713*a*. A linear actuation force may be applied to the woven or braided portion 732*a* by way of a pull wire 734*a*. Pull wires are commonplace in the field of percutaneous intervention and a skilled artisan would be familiar with their use. In the first embodiment, one or more pull wires 734*a*, or a combined bundle of pull wires, are attached to the distal end of catheter 702*a*. As an axial force is applied on the pull wire(s) 734*a*, the catheter expands in the radial direction R, while simultaneously reducing length in the axial direction A. In this way, the distal end 712*a* of catheter 702*a* can expand its inner diameter from a first inner diameter to a second, larger, inner diameter, in order to ingest a clot. When the axial force is removed, the braided or woven portion 732*a* is allowed to freely elongate and return to its native state (i.e., its first inner diameter) before the device is retracted from the body. For example, the first inner diameter D4 of distal end may be 0.05 inches to 0.35 inches and the inner diameter D5 of distal opening may be 0.10 inches to 0.75 inches. Stated another way, the distal end of the aspiration catheter 702*a* can transition from a first state or native state having a first outside diameter to the enlarged state having a second outside diameter that is larger than the first outside diameter, where each of the first outside diameter and the second outside diameter can be selected from a French size in a range between about 3 Fr and about 26 Fr, or any French size between 3 Fr and 26 Fr.

Figure 17A:
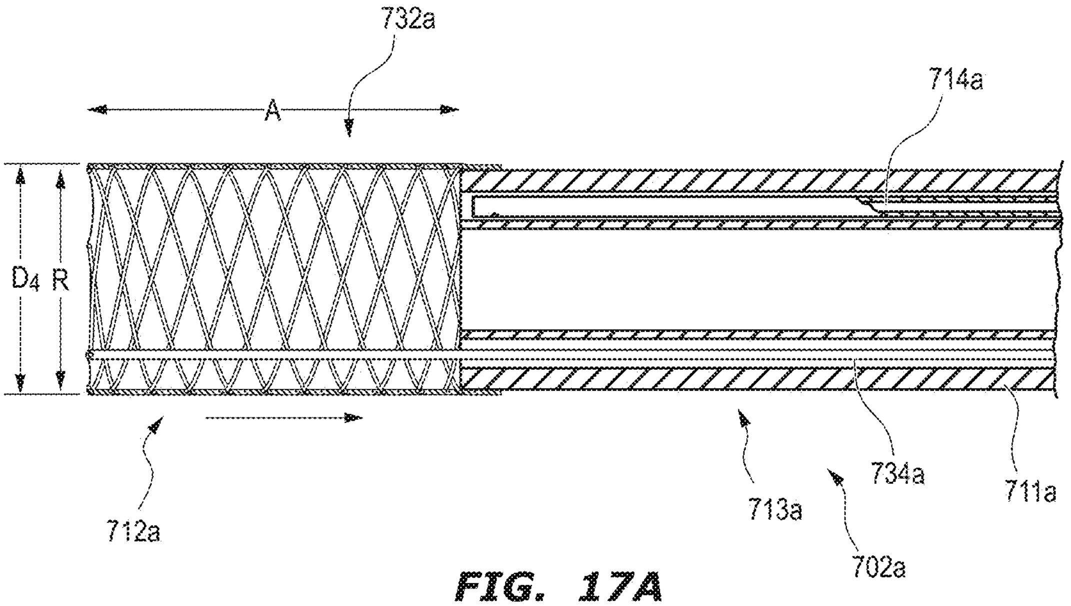
FIGS. 17A and 17B are sectional views of an exemplary aspiration catheter comprising a woven or braided portion configured to adopt an altered inner diameter upon application of an axial force according to an implementation of the present disclosure.
Figure 17B:
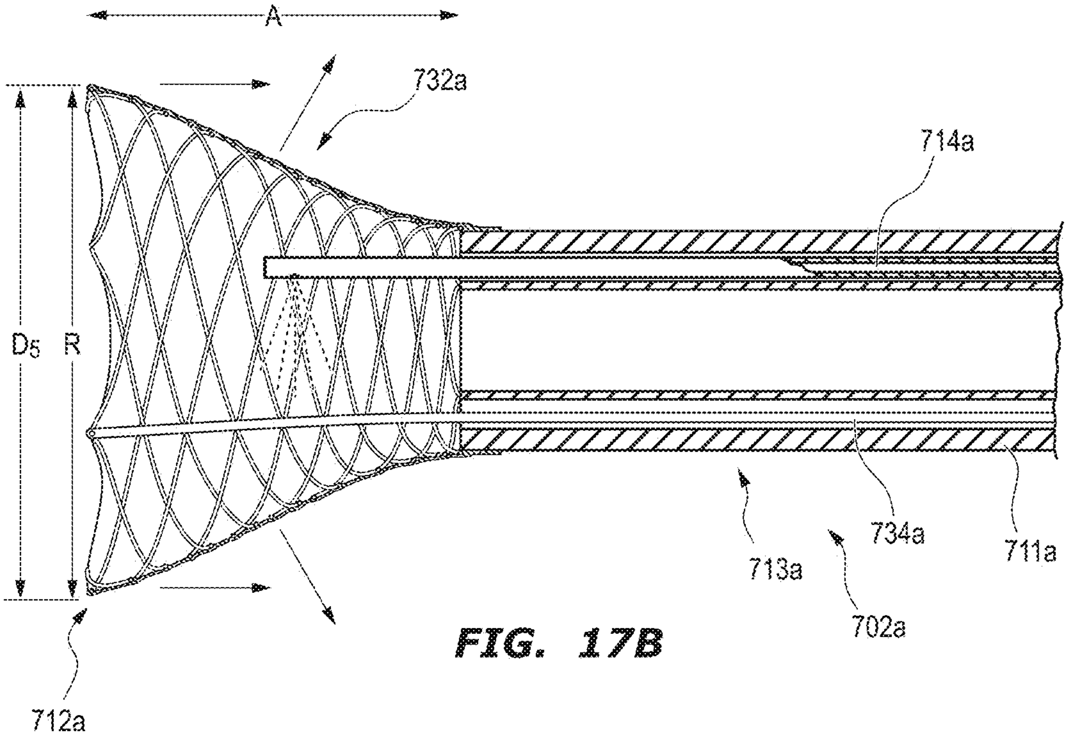
Figure 18A:
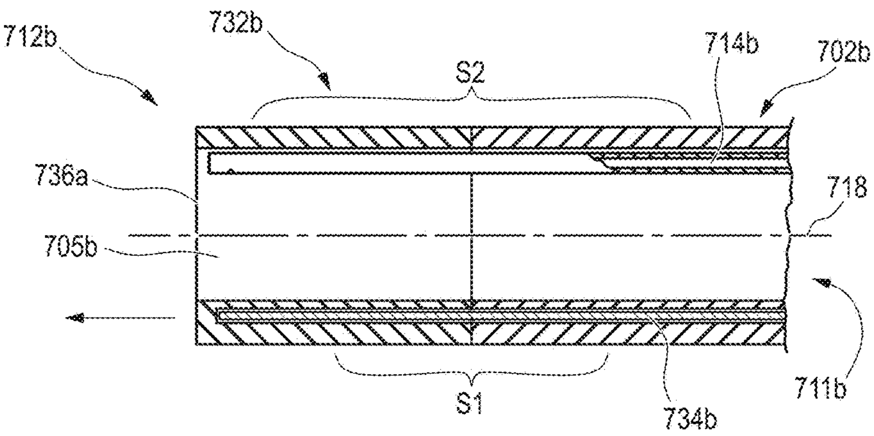
FIGS. 18A and 18B are sectional views of an exemplary aspiration catheter comprising a woven or braided portion configured to adopt a slanted distal tip upon actuation according to an implementation of the present disclosure.
Figure 18B:
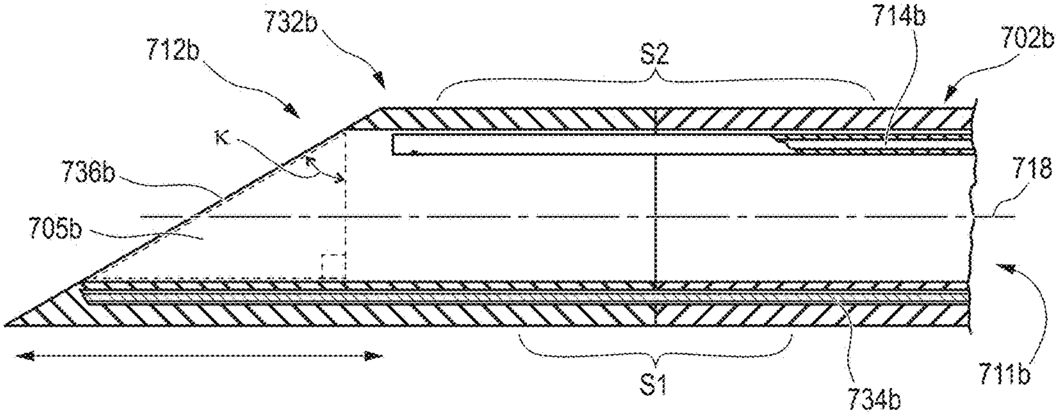
Figure 18C:
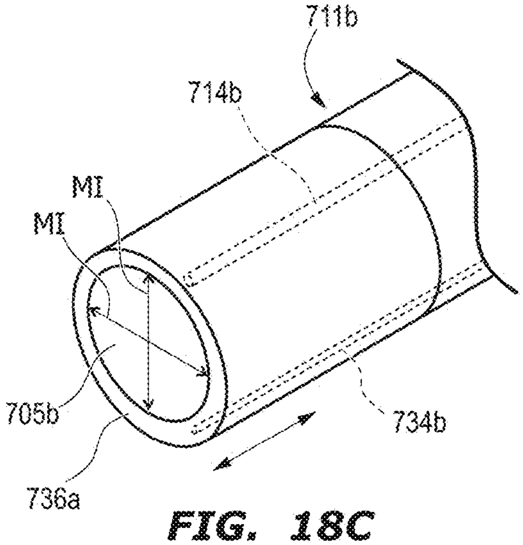
FIGS. 18C-18D are partial perspective views of an exemplary aspiration catheter comprising a woven or braided portion configured to adopt a slanted distal tip upon actuation according to an implementation of the present disclosure.
Figure 18D:
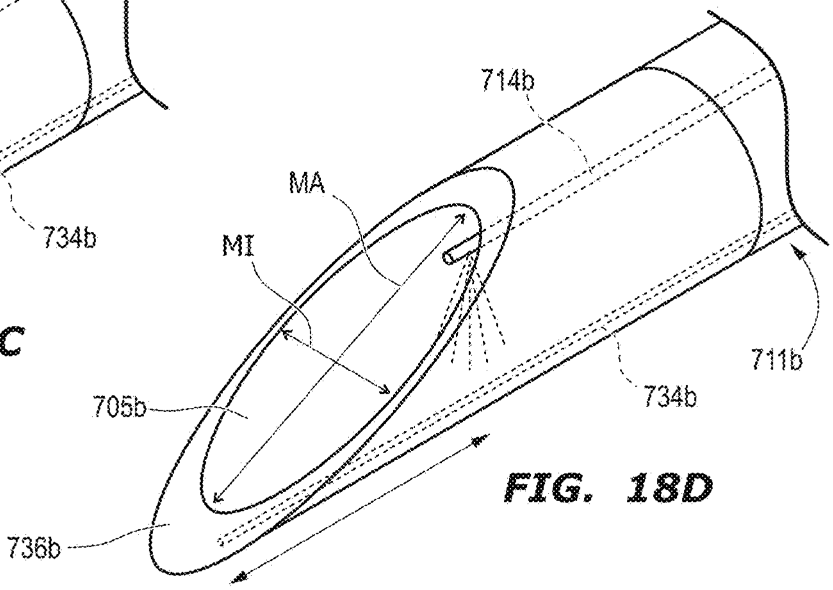

The disclosure related to the aspiration catheters and the tissue encroachment prevention assemblies described herein are also applicable to the tissue encroachment prevention assembly and the aspiration catheter of FIG. 17A-17B.

In the second embodiment, shown in FIG. 18A-18D, catheter 702*b* comprises a woven or braided portion 732*b* at its distal end 712*b* and a hypotube portion 711*b*, such as that discussed with reference to FIGS. 9-13B, at its proximal end 713*b*. A linear actuation force may be applied to the woven or braided portion 732*b* by way of an actuator 734*b*. When this occurs, the distal tip 736 is reshaped (from 736*a* to 736*b*) such that one side (S1) of catheter 702*b* becomes longer than the opposite side (S2), in order to achieve a larger diameter for distal opening 705*b* without changing the catheter French size. Additionally, the jet spray location from supply tube **714*b* is positioned towards the shorter side (S2) of the catheter tip 736*b*. The supply tube 714*b* may be axially moveable or may remain in a fixed position during reshaping of the distal tip 736. As illustrated in FIGS. 18A-18D, the slant tip 736*b* the distal opening 705*b* having an oval shape, with a dimension along a major axis $M_A$ being larger than the distal opening 705*b* with a tip 736*a* having an distal most surface approximating a plane lying generally perpendicular to a longitudinal axis 718. The minor axis $M_I$ dimension of the distal opening 705*b* with the slant tip 736*b* can be same or different from that of the distal opening 705*b* with the tip 736*a*, which has a generally uniform diameter. $M_A$ is calculated utilizing the cosine equation with the optimal selected angle to maximize $M_A$ and the diameter of the catheter, which is equal to $M_I$. The cosine equation being cosine $\kappa = M_I/M_A$, wherein K is an angle. In one configuration, the dimension along the minor axis $M_I$ is about 1.5 inches and the dimension along the major axis $M_A$ is about 2.12 inches when K is 45 degrees. Thus, the inner diameter of the distal opening 705*b* may be enlarged without having to change the French size of catheter 702*b***.

The disclosure related to the aspiration catheters and the tissue encroachment prevention assemblies described herein are also applicable to the tissue encroachment prevention assembly and the aspiration catheter of FIGS. 18A-18D.

Although the systems for aspirating thrombus described herein are predominantly focused on aspiration, the systems may also, or alternatively, be configured for injecting or infusing fluids, with or without drugs, and may incorporate related features described in U.S. Pat. No. 10,716,583, issued Jul. 21, 2020, and entitled, "Systems and Methods for Removal of Blood and Thrombotic Material" and U.S. Pat. No. 10,492,805, issued Dec. 3, 2019, and entitled, "Systems and Methods for Thrombosis and Delivery of an Agent."

It is contemplated that various combinations or sub-combinations of the specific features and aspects of the embodiments disclosed above may be made and still fall within one or more of the embodiments. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed embodiments. Thus, it is intended that the scope of the present disclosure herein disclosed should not be limited by the particular disclosed embodiments described above. Moreover, while the present disclosure is susceptible to various modifications, and alternative forms, specific examples thereof have been shown in the drawings and are herein described in detail. It should be understood, however, that the present disclosure is not to be limited to the particular forms or methods disclosed, but to the contrary, the present disclosure is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

Following are some further example embodiments of the invention. These are presented only by way of example and are not intended to limit the scope of the invention in any way. Further, any example embodiment can be combined with one or more of the example embodiments.

Embodiment 1. An aspiration catheter comprising an elongate shaft configured for placement within a blood vessel, a supply lumen and an aspiration lumen each extending along the shaft, the supply lumen having a proximal end and a distal end, and the aspiration lumen having a proximal end and a distal opening, an orifice at or near the distal end of the supply lumen, the orifice begin configured to allow injection of pressurized fluid into the aspiration lumen at or near the distal end of the aspiration lumen when the pressurized fluid is delivered through the supply lumen, and a tissue encroachment prevention assembly for preventing the blood vessel from being drawn into said aspiration lumen and coming into close proximity to the orifice of the supply lumen during aspiration.

Embodiment 2. The aspiration catheter of embodiment 1, wherein said tissue encroachment prevention assembly comprises a wide mouth tip located at or near the distal end of the aspiration catheter, the tip having a proximal end attached to the aspiration catheter and a distal opening, wherein the distal opening of the wide mouth tip has an inner diameter that is larger than the inner diameter of the aspiration lumen.

Embodiment 3. The aspiration catheter of any of embodiments 1-2, wherein the distal opening of the wide mouth tip has an inner diameter of at least 0.20 inches.

Embodiment 4. The aspiration catheter of any of embodiments 1-3, wherein the orifice is placed at a distance of at least 0.035 inches from the distal opening of the wide mouth tip.

Embodiment 5. The aspiration catheter of any of embodiments 1-4, further comprising one or more additional supply lumens, each having an orifice configured to allow injection of pressurized fluid into the aspiration lumen at or near the distal end of the aspiration lumen when the pressurized fluid is pumped through the supply lumen.

Embodiment 6. The aspiration catheter of any of embodiments 1-5, wherein the wide mouth tip is made of a block copolymer formed of a polyamide block and a polyether block and is heat bonded onto the distal end of the aspiration catheter.

Embodiment 7. The aspiration catheter of any of embodiments 1-6, wherein the elongate shaft is a laser cut hypotube laminated by a polymer.

Embodiment 8. The aspiration catheter of any of embodiments 1-7, wherein the elongate shaft is a multi-lumen extruded polymer shaft.

Embodiment 9. The aspiration catheter of any of embodiments 1-8, further comprising a radiopaque ring at or near the distal end of the aspiration catheter.

Embodiment 10. The aspiration catheter of any of embodiments 1-9, wherein the elongate shaft is formed as a multi-lumen shaft, such as an extruded polymer shaft.

Embodiment 11. The aspiration catheter of any of embodiments 1-10, wherein the tissue encroachment prevention assembly is glued or otherwise attached onto a distal end of the elongate shaft.

Embodiment 12. The aspiration catheter of any of embodiments 1-11, wherein the wide mouth tip is essentially cylindrical in shape.

Embodiment 13. The aspiration catheter of any of embodiments 1-12, wherein the wide mouth tip is essentially conical in shape.

Embodiment 14. The aspiration catheter of any of embodiments 1-13, wherein the supply lumen does not extend into a lumen of the wide mouth tip.

Embodiment 15. The aspiration catheter of any of embodiments 1-14, wherein the supply lumen extends into a lumen of the wide mouth tip.

Embodiment 16. The aspiration catheter of any of embodiments 1-15, further comprising at least one additional supply lumen.

Embodiment 17. The aspiration catheter of any of embodiments 1-16, wherein said tissue encroachment prevention assembly comprises an expandable member located at or near the distal end of the aspiration catheter, the expandable member having a proximal end attached to the aspiration catheter and a distal opening, wherein the distal opening or end of the expandable member has an inner diameter that is larger than the inner diameter of the aspiration lumen.

Embodiment 18. The aspiration catheter of any of embodiments 1-17, wherein the expandable member comprises an expandable cage, skirt, or basket structure upon inflation of the expandable member.

Embodiment 19. The aspiration catheter of any of embodiments 1-18, further comprising a housing lumen configured to house a memory shape member that is configured to inflate the expandable member upon deployment of the memory shape member from the housing lumen.

Embodiment 20. The aspiration catheter of any of embodiments 1-19, wherein the memory shape member is a nitinol wire preformed to adopt a coiled configuration upon deployment from the housing lumen.

Embodiment 21. The aspiration catheter of any of embodiments 1-20, wherein the expandable member comprises an inflatable balloon.

Embodiment 22. The aspiration catheter of any of embodiments 1-21, further comprising a second supply lumen configured to supply a liquid infusion into the expandable member in order to inflate the expandable member.

Embodiment 23. The aspiration catheter of any of embodiments 1-22, wherein the expandable cage, skirt, or basket structure is made of nitinol, plastic, silicone, latex, or other polymer.

Embodiment 24. The aspiration catheter of any of embodiments 1-23, further comprising an outer sheath configured to house the expandable member until its deployment or inflation.

Embodiment 25. The aspiration catheter of any of embodiments 1-24, wherein the expandable member is configured to inflate upon retraction of the outer sheath.

Embodiment 26. The aspiration catheter of any of embodiments 1-25, wherein the elongate shaft comprises a woven or braided portion at the distal end of the elongate shaft and a hypotube portion at the proximal end of the elongate shaft.

Embodiment 27. The aspiration catheter of any of embodiments 1-26, wherein the expandable member comprises a woven or braided portion at the distal end of the elongate shaft, the remainder of the elongate shaft comprising a hypotube.

Embodiment 28. The aspiration catheter of any of embodiments 1-27, wherein the woven or braided portion of the elongate shaft is configured to expand in a radial direction when a linear actuation force is applied in an axial direction to the woven or braided portion.

Embodiment 29. The aspiration catheter of any of embodiments 1-28, further comprising a pull wire that is configured to apply a linear actuation force to the woven or braided material.

Embodiment 30. The aspiration catheter of any of embodiments 1-29, wherein the woven or braided portion is configured to expand an inner diameter of a distal opening of the woven or braided portion upon actuation of the pull wire in the axial direction.

Embodiment 31. The aspiration catheter of any of embodiments 1-30, further comprising a shape memory member operatively coupled to the expandable member.

Embodiment 32. The aspiration catheter of any of embodiments 1-31, further comprising an actuator, wherein the woven or braided portion is configured to reshape upon actuation of the actuator such that one side of the woven or braided portion is longer than the opposite side of the woven or braided portion and the distal tip of the woven or braided portion is changed from an edge tip to a slanted edge tip.

Embodiment 33. An aspiration catheter comprising an elongate shaft configured for placement within a blood vessel, the elongate shaft having a distal end with an opening at the distal end, a supply lumen and an aspiration lumen each extending along the shaft, the supply lumen having a proximal end and a distal end, and the aspiration lumen having a proximal end and a distal opening, an orifice near the distal end of the supply lumen, the orifice being configured to allow injection of pressurized fluid into the aspiration lumen at or near the distal end of the aspiration lumen when the pressurized fluid is delivered through the supply lumen; and a means for preventing the blood vessel from being drawn into the aspiration lumen and into close proximity to the orifice of the supply lumen during aspiration.

Embodiment 34. The aspiration catheter of embodiment 33, wherein means for preventing the blood vessel from being drawn into the aspiration lumen comprises a wide mouth tip located at or near the distal end of the aspiration catheter, the tip having a proximal end attached to the aspiration catheter and a distal opening.

Embodiment 35. The aspiration catheter of any of embodiments 33-34, wherein the distal opening of the wide mouth tip has an inner diameter that is larger than the inner diameter of the aspiration lumen.

Embodiment 36. The aspiration catheter of any of embodiment 33-35, wherein the wide mouth tip has an opening with an inner diameter of at least 0.20 inches.

Embodiment 37. An aspiration catheter comprising an elongate shaft configured for placement within a blood vessel, the elongate shaft having a distal end with an opening at the distal end, a supply lumen and an aspiration lumen each extending along an interior of the shaft, coextensive with the shaft, the supply lumen having a proximal end and a distal end, and the aspiration lumen having a proximal end and a distal opening, an orifice near the distal end of the supply lumen, the orifice being configured to allow injection of pressurized fluid into the aspiration lumen at or near the distal end of the aspiration lumen when the pressurized fluid is pumped through the supply lumen, and a tissue encroachment prevention assembly for preventing the blood vessel from being drawn into the aspiration lumen and into close proximity to the orifice of the supply lumen during aspiration, the tissue encroachment prevention assembly comprising at least one of a wide-mouth tip and an expandable member located at or near the distal end of the aspiration catheter.

Embodiment 38. The aspiration catheter of embodiment 37, wherein the wide-mouth tip has a proximal end attached to the aspiration catheter and a distal opening.

Embodiment 39. The aspiration catheter of any of embodiments 37-38, wherein the distal opening of the wide mouth tip has an inner diameter that is larger than the inner diameter of the aspiration lumen.

Embodiment 40. The aspiration catheter of any of embodiments 37-39, wherein the wide mouth tip has an opening with an inner diameter of at least 0.20 inches.

Embodiment 41. The aspiration catheter of any of embodiments 37-40, wherein the orifice is placed at a distance of at least 0.01 inches from the distal opening of the wide mouth tip.

Embodiment 42. The aspiration catheter of any of embodiments 37-41, further comprising one or more additional supply lumens, each having an orifice configured to allow injection of pressurized fluid into the aspiration lumen at or near the distal end of the aspiration lumen when the pressurized fluid is pumped through the supply lumen.

Embodiment 43. The aspiration catheter of any of embodiments 37-42, wherein the wide-mouth tip is made of a block copolymer formed of a polyamide block and a polyether block and is heat bonded onto the distal end of the aspiration catheter.

Embodiment 44. The aspiration catheter of any of embodiments 37-43, wherein the elongate shaft is a laser cut hypotube laminated by a polymer.

Embodiment 45. The aspiration catheter of any of embodiments 37-44, wherein the elongate shaft is a multi-lumen extruded polymer shaft.

Embodiment 46. The aspiration catheter of any of embodiments 37-45, further comprising a radiopaque ring near the distal end of the aspiration catheter.

Embodiment 47. A system for aspirating thrombus, comprising: an aspiration catheter comprising: an elongate shaft configured for placement within a blood vessel of a subject; a supply lumen and an aspiration lumen each extending along an interior of the elongate shaft; and an orifice at or near a distal end of the supply lumen, the orifice being configured to allow the injection of pressurized fluid into the aspiration lumen at or near the distal end of the aspiration lumen when the pressurized fluid is caused or allowed to flow through the supply lumen; a tubing set comprising a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source; a pressurization element configured to couple to the tubing set and further configured to pressurize fluid from the first fluid source or allow pressurized fluid from the first fluid source to be transferred to the supply lumen, such that the pressurized fluid is capable of flowing through the supply lumen from the proximal end of the supply lumen to the orifice at or near the distal end of the supply lumen; and a means for preventing the blood vessel from being drawn into the aspiration lumen and into close proximity to the orifice of the supply lumen during aspiration.

Embodiment 48. The system for aspirating thrombus of embodiment 47, wherein the means for preventing the blood vessel from being drawn into the aspiration lumen and into close proximity to the orifice of the supply lumen during aspiration comprises a wide mouth tip located at the distal end of the aspiration catheter.

Embodiment 49. The system for aspirating thrombus of any of embodiments 47-48, wherein the means for preventing the blood vessel from being drawn into the aspiration lumen and into close proximity to the orifice of the supply lumen during aspiration comprises an expandable member located at the distal end of the aspiration catheter.

Embodiment 50. A system for aspirating thrombus, comprising: an aspiration catheter comprising: an elongate shaft configured for placement within a blood vessel of a subject; a supply lumen and an aspiration lumen each extending along an interior of the elongate shaft; and an orifice at or near a distal end of the supply lumen, the orifice being configured to allow the injection of pressurized fluid into the aspiration lumen at or near the distal end of the aspiration lumen when the pressurized fluid is caused or allowed to flow through the supply lumen; a tubing set comprising a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source; a pressurization element configured to couple to the tubing set and further configured to pressurize fluid from the first fluid source or allow pressurized fluid from the first fluid source to be transferred to the supply lumen, such that the pressurized fluid is capable of flowing through the supply lumen from the proximal end of the supply lumen to the orifice at or near the distal end of the supply lumen; and a tissue encroachment prevention assembly for preventing the blood vessel from being drawn into the aspiration lumen and into close proximity to the orifice of the supply lumen during aspiration.

Embodiment 51. The system for aspirating thrombus of embodiment 50, wherein the tissue encroachment prevention assembly for preventing the blood vessel from being drawn into the aspiration lumen and into close proximity to the orifice of the supply lumen during aspiration comprises a wide mouth tip located at the distal end of the aspiration catheter.

Embodiment 52. The system for aspirating thrombus of any of embodiments 50-51, wherein the tissue encroachment prevention assembly for preventing the blood vessel from being drawn into the aspiration lumen and into close proximity to the orifice of the supply lumen during aspiration comprises an expandable member located at the distal end of the aspiration catheter.

Embodiment 53. An aspiration catheter comprising: an elongate shaft configured for placement within a blood vessel; a supply lumen and an aspiration lumen each extending along an interior of the shaft, coextensive with the shaft, the supply lumen having a proximal end and a distal end, and the aspiration lumen having a proximal end and a distal opening; an orifice at or near the distal end of the supply lumen, the orifice configured to allow injection of pressurized fluid into the aspiration lumen at or near the distal end of the aspiration lumen when the pressurized fluid is pumped through the supply lumen; and a means for preventing the blood vessel from being drawn into said aspiration lumen and coming into close proximity to the orifice of the supply lumen during aspiration, said means comprising: a wide mouth tip located at or near the distal end of the aspiration catheter, the tip having a proximal end attached to the aspiration catheter and a distal opening; wherein the distal opening of the wide mouth tip has an inner diameter that is larger than the inner diameter of the aspiration lumen.

Embodiment 54. An aspiration catheter comprising an elongate shaft configured for placement within a blood vessel; a supply lumen and an aspiration lumen each extending along an interior of the shaft, coextensive with the shaft, the supply lumen having a proximal end and a distal end, and the aspiration lumen having a proximal end and a distal opening; an orifice at or near the distal end of the supply lumen, the orifice configured to allow injection of pressurized fluid into the aspiration lumen at or near the distal end of the aspiration lumen when the pressurized fluid is pumped through the supply lumen; and a means for preventing the blood vessel from being drawn into said aspiration lumen and coming into close proximity to the orifice of the supply lumen during aspiration, said means comprising: an expandable member located at or near the distal end of the aspiration catheter, the expandable member having a proximal end attached to the aspiration catheter and a distal opening; wherein the distal opening of the expandable member has an inner diameter that is larger than the inner diameter of the aspiration lumen when the expandable member is in an inflated state.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. An aspiration catheter comprising:

an elongate shaft configured for placement within a blood vessel;

a supply lumen and an aspiration lumen each extending along the shaft, the supply lumen having a proximal end and a distal end, and the aspiration lumen having a proximal end and a distal opening;

an orifice at or near the distal end of the supply lumen, the orifice being configured to allow injection of pressurized fluid into the aspiration lumen at or near the distal end of the aspiration lumen when the pressurized fluid is delivered through the supply lumen; and a tissue encroachment prevention assembly for preventing the blood vessel from being drawn into said aspiration lumen and coming into close proximity to the orifice of the supply lumen during aspiration, the tissue encroachment prevention assembly comprising a wide-mouth tip having a proximal end portion coupled to the elongate shaft, a distal end portion, a lumen extending through the wide-mouth tip, and a sidewall extending from the proximal end portion toward the distal end portion, the sidewall including a flared portion that expands radially outwardly in a distal direction, wherein the supply lumen is defined at least in part by a supply tube extending partially through the lumen of the wide-mouth tip, the supply tube having a distal region that bends radially outwardly so as to follow the flared portion of the sidewall so as to position the orifice to direct the pressurized fluid into the lumen of the wide-mouth tip.

2. The aspiration catheter of claim 1, wherein the distal end portion of the wide-mouth tip has a distal opening, the distal opening of the wide mouth tip having an inner diameter that is larger than the inner diameter of the aspiration lumen.

3. The aspiration catheter of claim 2, wherein the distal opening of the wide mouth tip has an inner diameter of at least 0.20 inches.

4. The aspiration catheter of claim 2, wherein the wide mouth tip is essentially cylindrical or conical in shape.

5. The aspiration catheter of claim 1, wherein the orifice is placed at a distance of at least 0.035 inches from the distal opening of the wide mouth tip.

6. The aspiration catheter of claim 1, wherein the wide-mouth tip comprises an expandable member, the expandable member having a distal opening, the distal opening or end of the expandable member having an inner diameter that is larger than the inner diameter of the aspiration lumen when expanded.

7. The aspiration catheter of claim 6, wherein the expandable member comprises an expandable cage, skirt, or basket structure upon inflation of the expandable member.

8. The aspiration catheter of claim 6, further comprising an outer sheath configured to house the expandable member until its deployment or inflation, wherein the expandable member is configured to inflate upon retraction of the outer sheath.

9. The aspiration catheter of claim 6, further comprising a housing lumen configured to house a memory shape member that is configured to inflate the expandable member upon deployment of the memory shape member from the housing lumen.

10. The aspiration catheter of claim 6, wherein the expandable member comprises an inflatable balloon, and further comprising a second supply lumen configured to supply a liquid infusion into the expandable member in order to inflate the expandable member.

11. The aspiration catheter of claim 6, wherein the expandable member comprises a woven or braided portion at the distal end of the elongate shaft, wherein the woven or braided portion of the elongate shaft is configured to expand in a radial direction when a linear actuation force is applied in an axial direction to the woven or braided portion.

12. An aspiration catheter comprising:

an elongate shaft configured for placement within a blood vessel, the elongate shaft having a distal end with an opening at the distal end;

a supply lumen and an aspiration lumen each extending along an interior of the shaft, coextensive with the shaft, the supply lumen having a proximal end and a distal end, and the aspiration lumen having a proximal end and a distal opening;

an orifice near the distal end of the supply lumen, the orifice being configured to allow injection of pressurized fluid into the aspiration lumen at or near the distal end of the aspiration lumen when the pressurized fluid is pumped through the supply lumen;

a tissue encroachment prevention assembly for preventing the blood vessel from being drawn into the aspiration lumen and into close proximity to the orifice of the supply lumen during aspiration, the tissue encroachment prevention assembly comprising an expandable member located at or near the distal end of the aspiration catheter, the expandable member comprising a channel and being configured to move between a collapsed configuration and an expanded configuration; and a memory shape member that is selectively advanceable from the elongate shaft and into the channel of the expandable member to move the expandable member from the collapsed configuration to the expanded configuration and selectively withdrawable from the channel and into the elongate shaft to allow the expandable member to return toward the collapsed configuration.

13. The aspiration catheter of claim 12, wherein the expandable member has a proximal end attached to the elongate shaft and a distal opening.

14. The aspiration catheter of claim 12, wherein the distal opening of the expandable member has an inner diameter that is larger than the inner diameter of the aspiration lumen.

15. An aspiration catheter comprising:

an elongate shaft configured for placement within a blood vessel, the elongate shaft having a distal end with an opening at the distal end;

a supply lumen and an aspiration lumen each extending along an interior of the shaft, coextensive with the shaft, the supply lumen having a proximal end and a distal end, and the aspiration lumen having a proximal end and a distal opening;

an orifice near the distal end of the supply lumen, the orifice being configured to allow injection of pressurized fluid into the aspiration lumen at or near the distal end of the aspiration lumen when the pressurized fluid is pumped through the supply lumen;

a woven or braided portion at the distal end of the elongate shaft; and an actuator configured to apply a linear actuation force in an axial direction to the woven or braided portion, wherein, upon actuation of the actuator, the woven or braided portion is configured to reshape a distal tip of the woven or braided portion from a configuration in which a distal-most surface of the distal tip approximates a plane lying generally perpendicular to a longitudinal axis of the aspiration catheter to a slanted distal tip configuration in which a first side of the distal tip is longer than an opposite second side of the distal tip, wherein the distal opening has an oval shape in the slanted distal tip configuration with a dimension along a major axis that is larger than a corresponding dimension of the distal opening before the distal tip is reshaped to the slanted distal tip configuration, and wherein a jet spray location from the supply lumen is positioned toward the second side of the distal tip.

16. The aspiration catheter of claim 15, wherein the elongate shaft comprises a hypotube portion proximal to the woven or braided portion.

17. The aspiration catheter of claim 15, wherein the supply lumen is defined at least in part by a supply tube, and wherein the supply tube is configured to move axially when the woven or braided portion is reshaped to the slanted distal tip configuration.

18. The aspiration catheter of claim 15, wherein the supply lumen is defined at least in part by a supply tube, and wherein the supply tube is configured to remain fixed while the woven or braided portion is reshaped to the slanted distal tip configuration.

19. The aspiration catheter of claim 15, wherein the second side of the distal tip is a shorter side of the distal tip in the slanted distal tip configuration, and wherein the jet spray location is positioned toward the shorter side of the distal tip.

20. The aspiration catheter of claim 19, wherein the distal opening has a minor axis in the slanted distal tip configuration, and wherein a dimension of the distal opening along the minor axis is the same as or different from a diameter of the distal opening before the distal tip is reshaped to the slanted distal tip configuration.

* * * * *